(12) United States Patent
Kuriyama

(10) Patent No.: US 6,270,326 B1
(45) Date of Patent: Aug. 7, 2001

(54) TRANSFUSION DEVICE AND LIQUID SUPPLY TUBE

(75) Inventor: Hiroshi Kuriyama, Shimosuwa-machi (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/284,844

(22) PCT Filed: Aug. 31, 1998

(86) PCT No.: PCT/JP98/03914

§ 371 Date: Apr. 21, 1999

§ 102(e) Date: Apr. 21, 1999

(87) PCT Pub. No.: WO99/11309

PCT Pub. Date: Mar. 11, 1999

(30) Foreign Application Priority Data

| Aug. 29, 1997 | (JP) | 9-234925 |
| Aug. 29, 1997 | (JP) | 9-234926 |
| Aug. 29, 1997 | (JP) | 9-234927 |
| Oct. 24, 1997 | (JP) | 9-293057 |

(51) Int. Cl.⁷ ................................ F05B 45/06
(52) U.S. Cl. ........................................ 417/477.4
(58) Field of Search .................. 417/477, 476, 417/477.3, 477.4, 477.5

(56) References Cited

U.S. PATENT DOCUMENTS

| 1,874,667 | * | 8/1932 | Wada | 417/477.3 |
| 2,015,123 | * | 9/1935 | Pennel | 417/477.4 |
| 2,752,860 | * | 7/1956 | Waldin | 417/477.3 |
| 3,652,192 | * | 3/1972 | Kramer et al. | 418/125 |
| 4,482,347 | * | 11/1984 | Borsanyi | 604/153 |
| 4,558,991 | * | 12/1985 | Barr | 417/199.1 |
| 4,728,265 | | 3/1988 | Cannon | 417/363 |
| 4,854,836 | | 8/1989 | Borsanyi | 417/474 |
| 5,281,210 | | 1/1994 | Burke et al. | 604/891.1 |

FOREIGN PATENT DOCUMENTS

| 61-55393 | 11/1986 | (JP) . |
| 62-191681 | 8/1987 | (JP) . |
| 62-258178 | 11/1987 | (JP) . |
| 63-209662 | 8/1988 | (JP) . |
| 6-48675 | 7/1994 | (JP) . |
| 7-509168 | 10/1995 | (JP) . |

* cited by examiner

*Primary Examiner*—Timothy S. Thorpe
*Assistant Examiner*—Ehud Gartenberg

(57) ABSTRACT

The structural complexity of conventional transfusing devices is eliminated, and it is made possible to supply a minute amount of liquid medicine with high accuracy with a simple structure, whereby a portable transfusion pump is realized. A cylindrical rotary drive member (24) equipped with a rotation shaft (23) is arranged opposite to a support plate (22), and a liquid supply tube (16) is arranged between the support plate (22) and the rotary drive member (24). On the outer peripheral surface of the rotary drive member (24), a pressing protrusion (24a) extending spirally around the axis is formed integrally. A flexible sheet (25) is provided between the rotary drive member (24) and the liquid supply tube (16). The upper and lower ends of this sheet (25) are directly or indirectly fixed to a base (10) and the support plate (22).

1 Claim, 20 Drawing Sheets

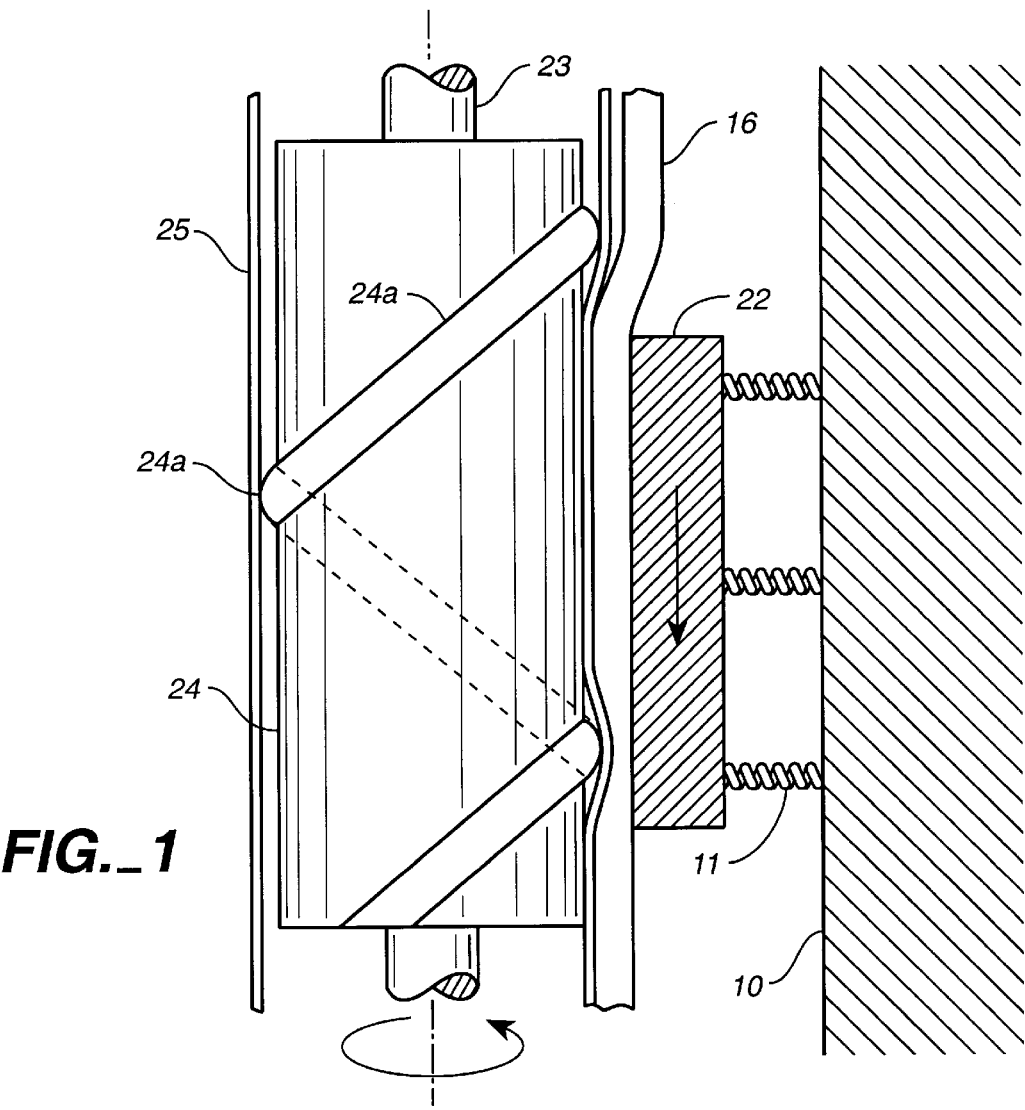
FIG._1
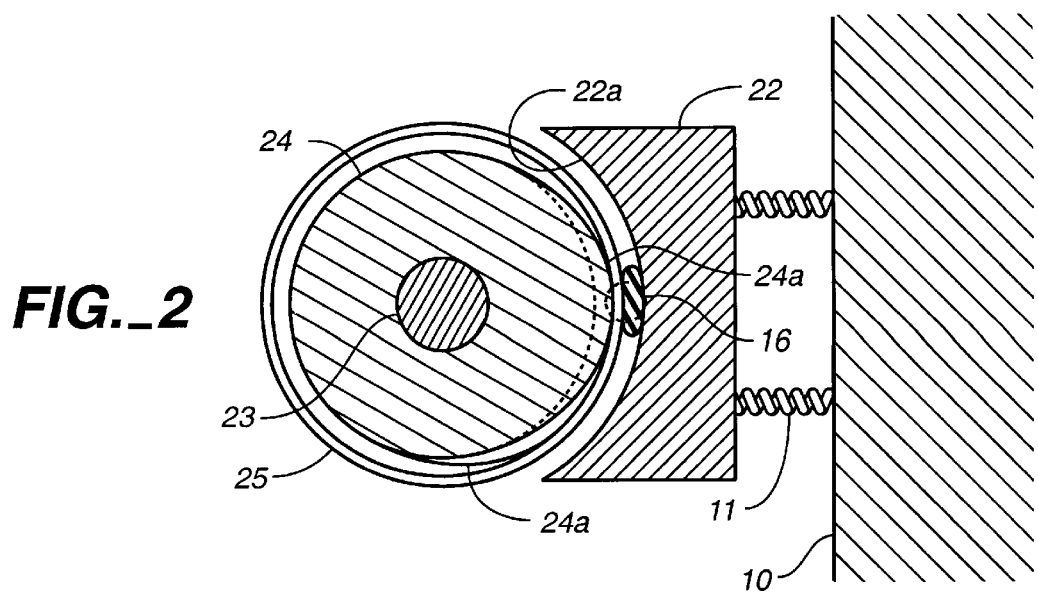
FIG._2

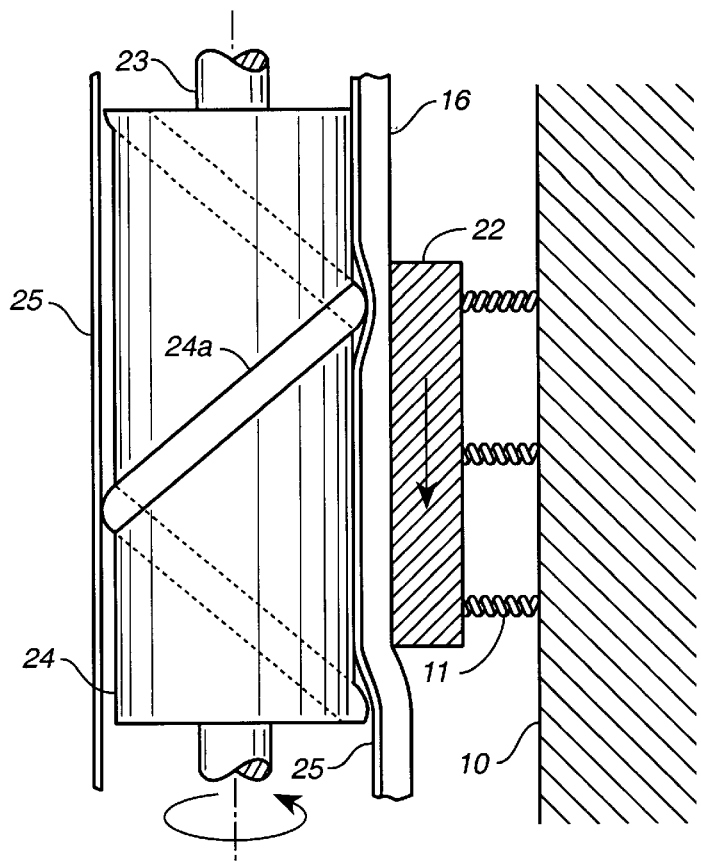
FIG._3
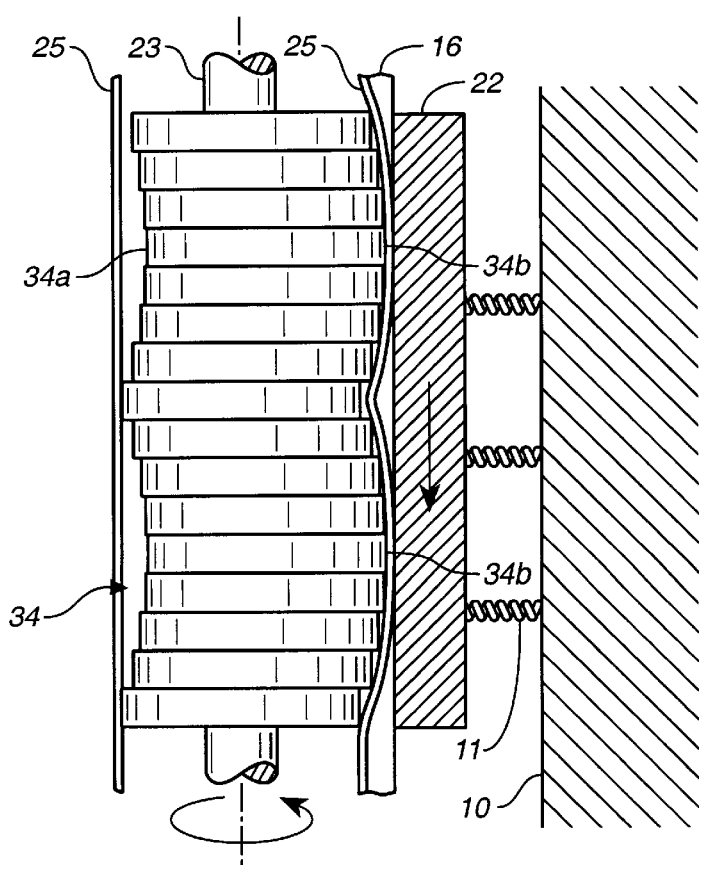
FIG._4

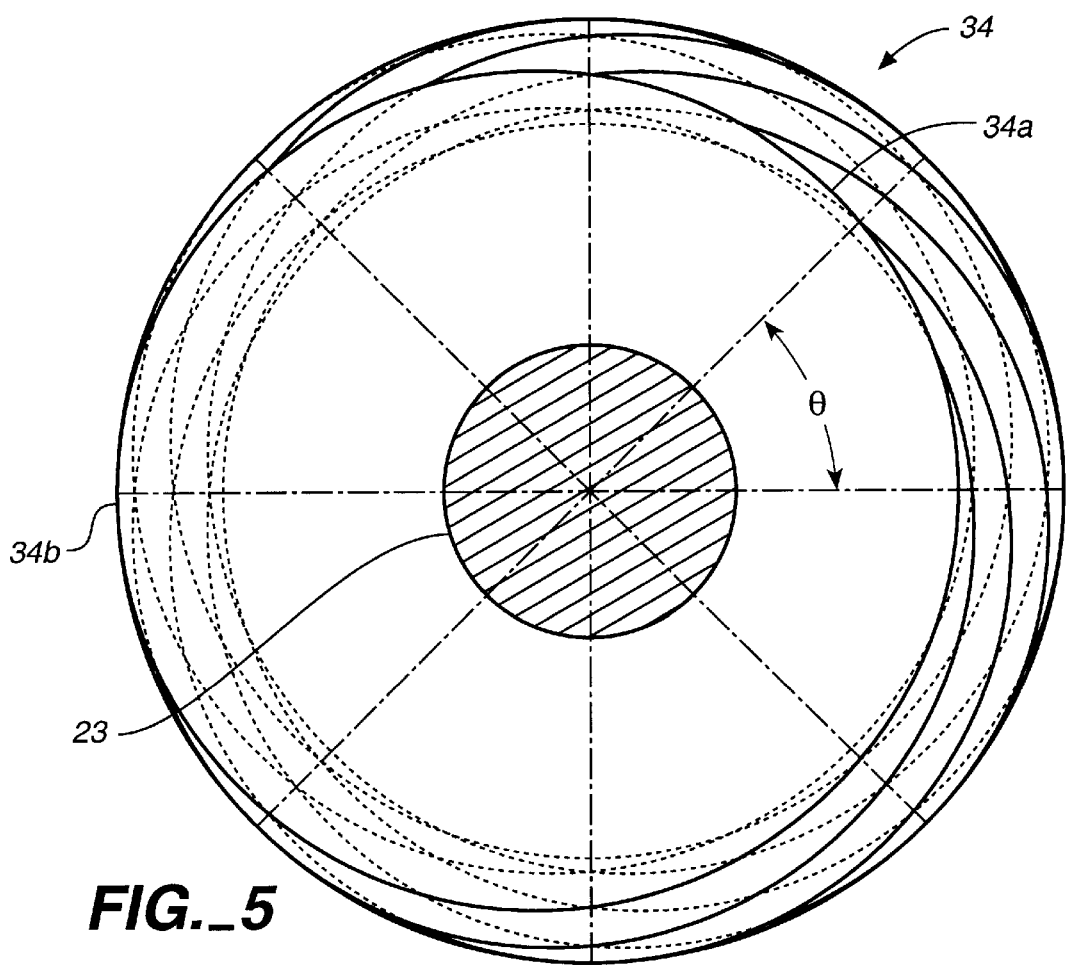
FIG._5
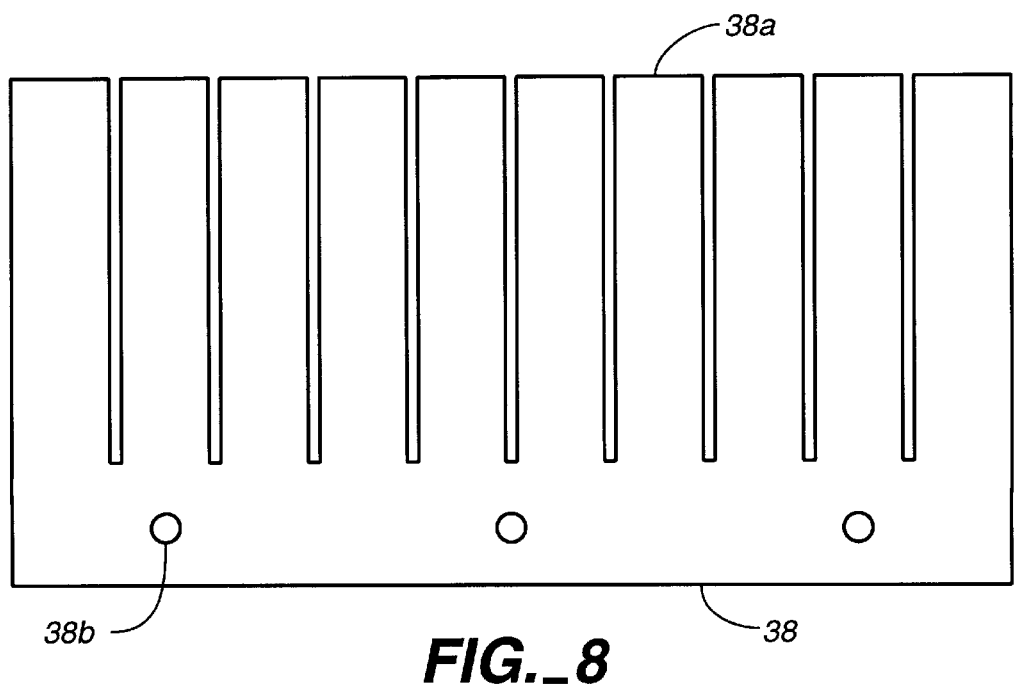
FIG._8

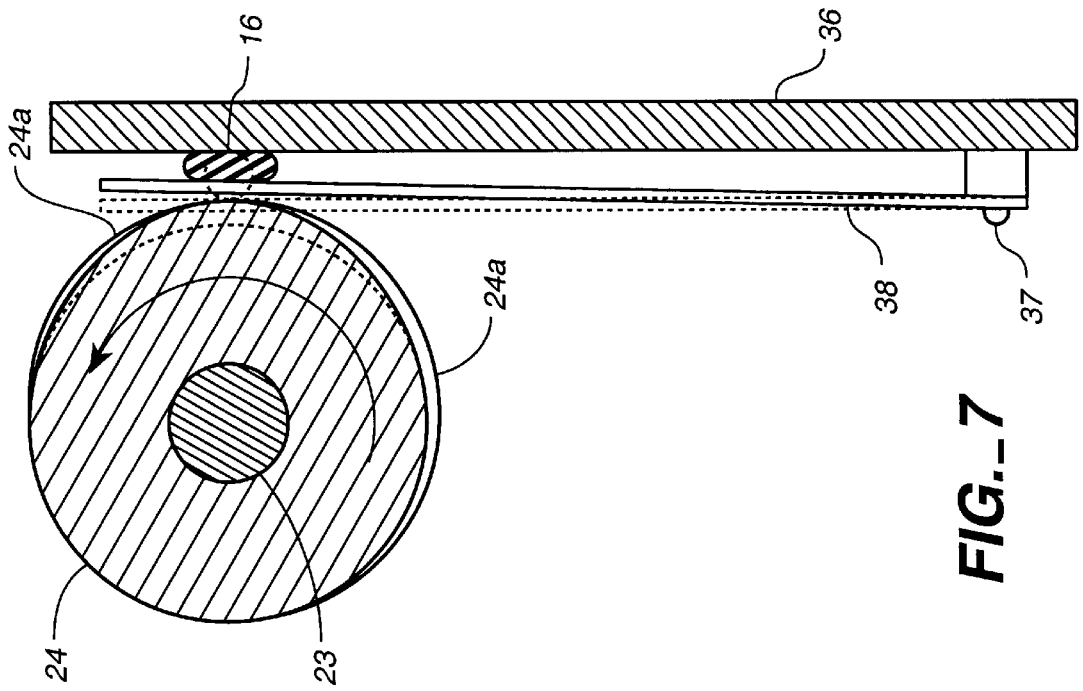
FIG._7
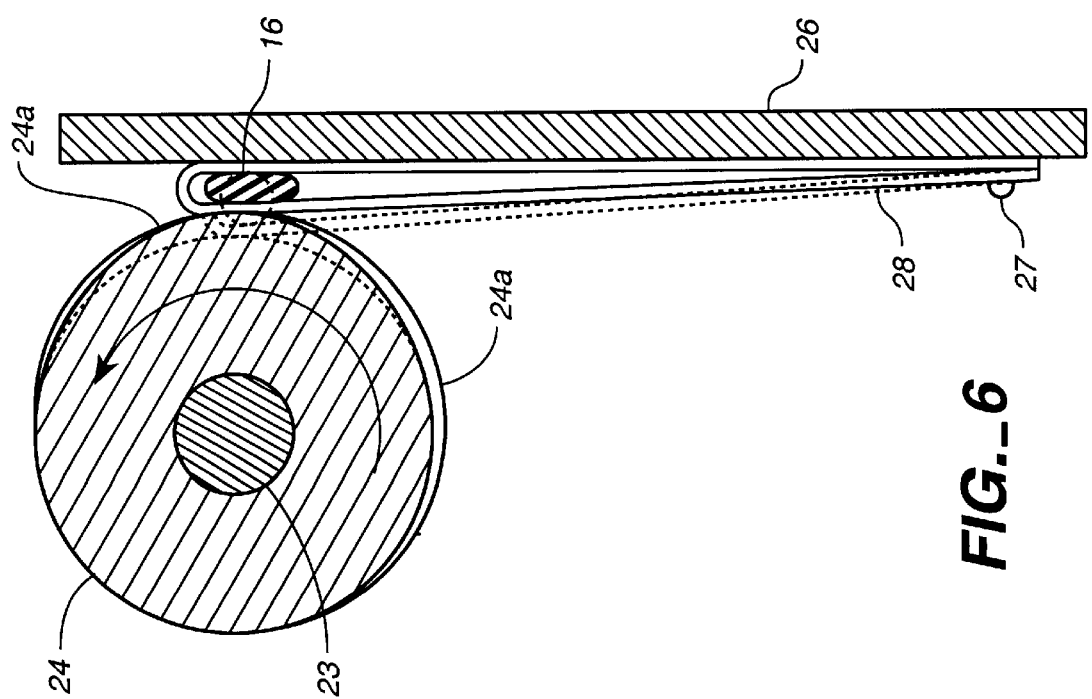
FIG._6

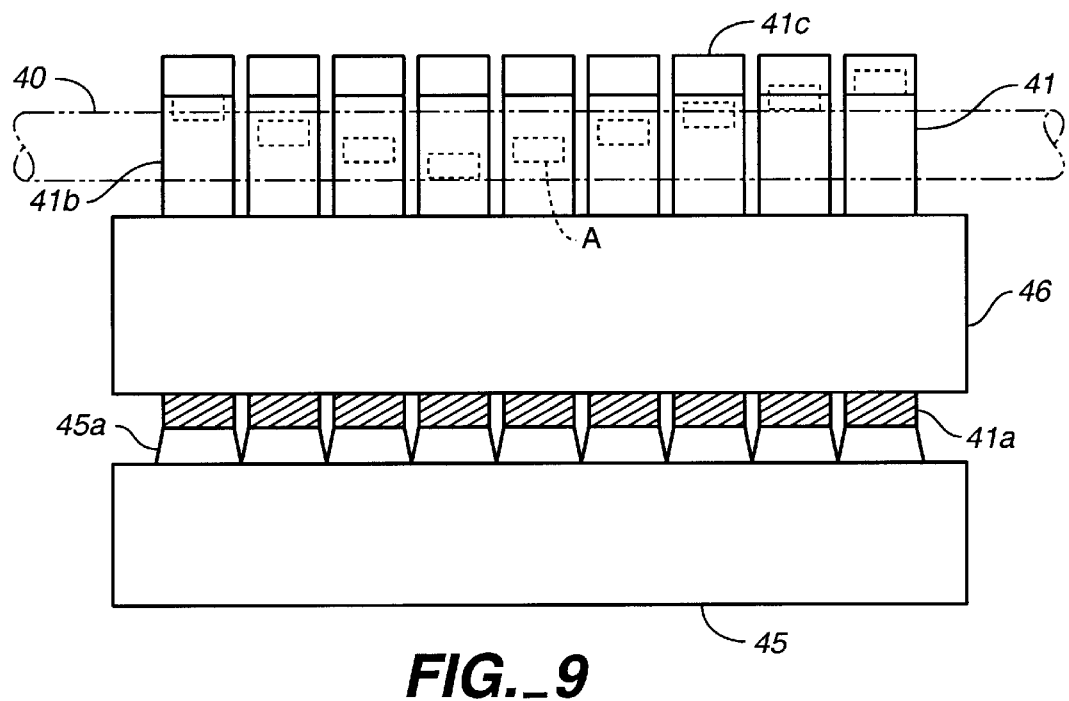
FIG._9
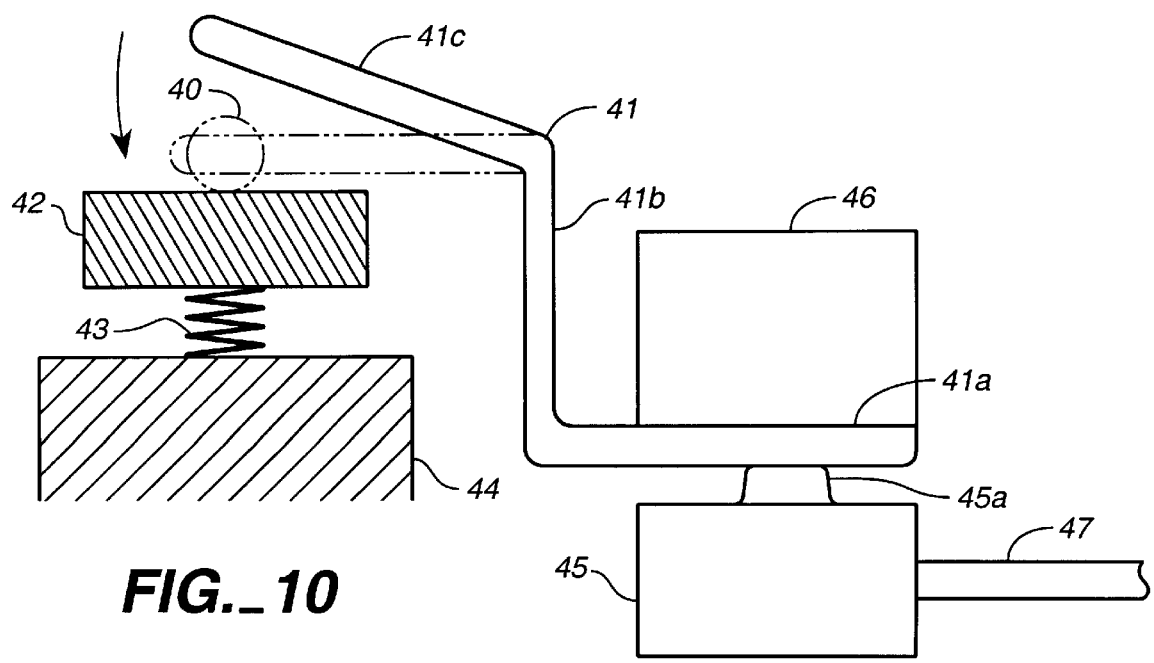
FIG._10

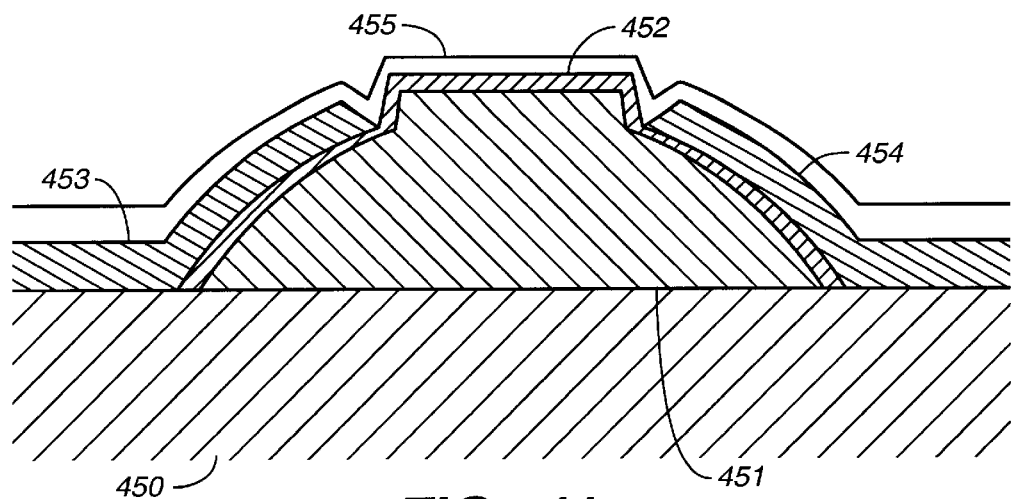
FIG._11
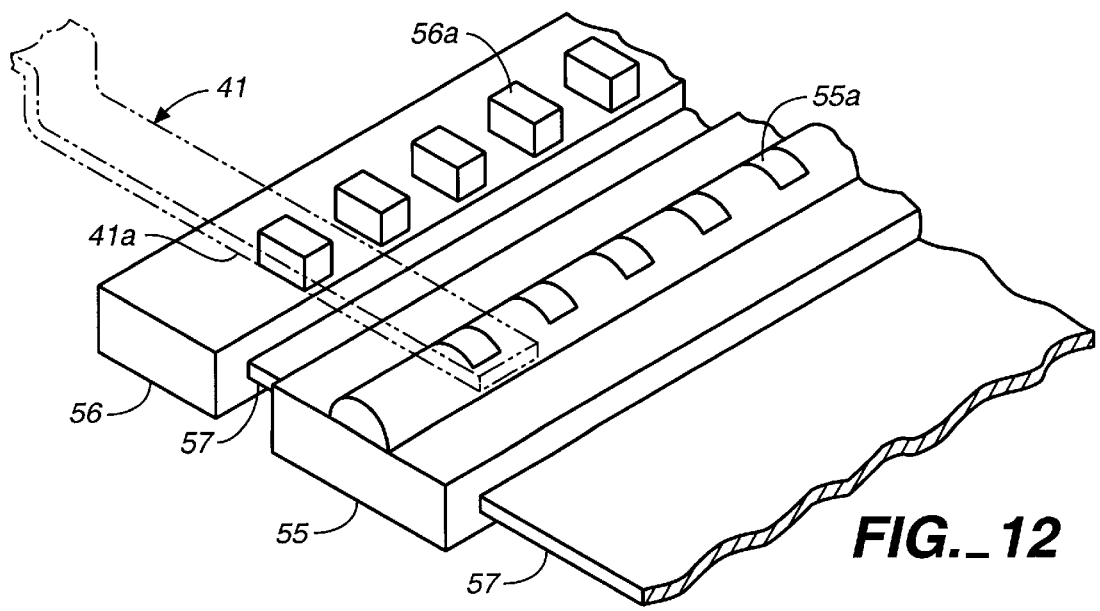
FIG._12

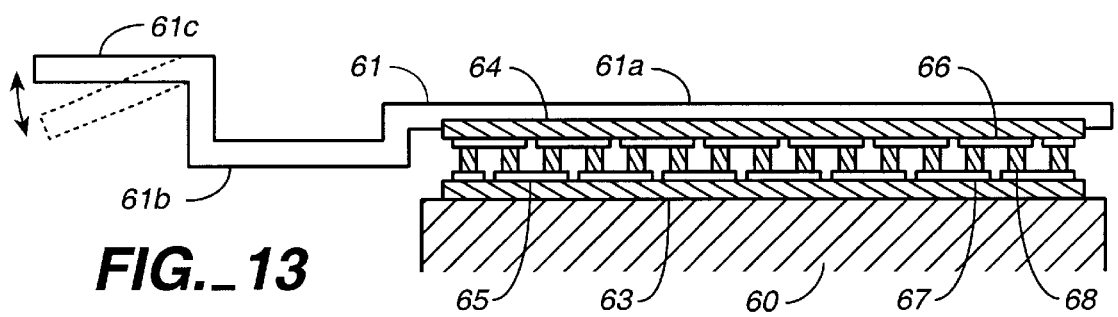
FIG._13
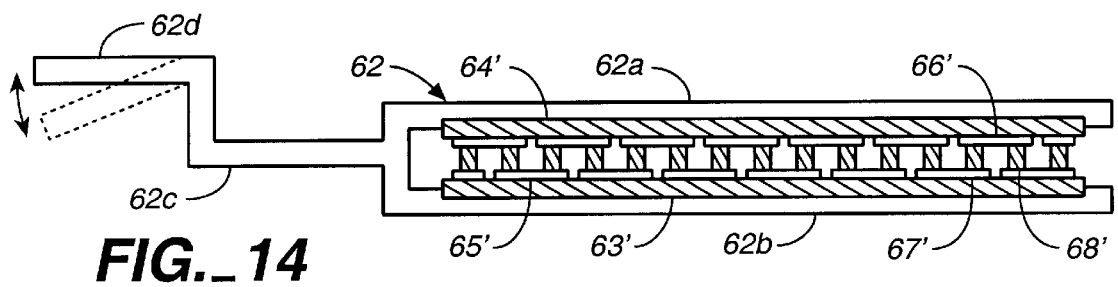
FIG._14
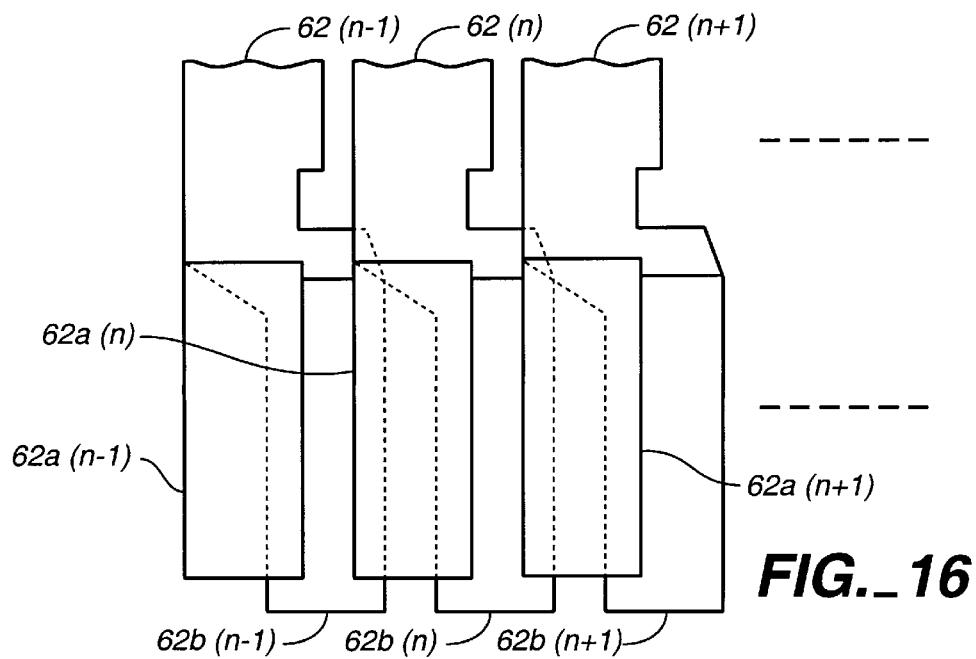
FIG._16

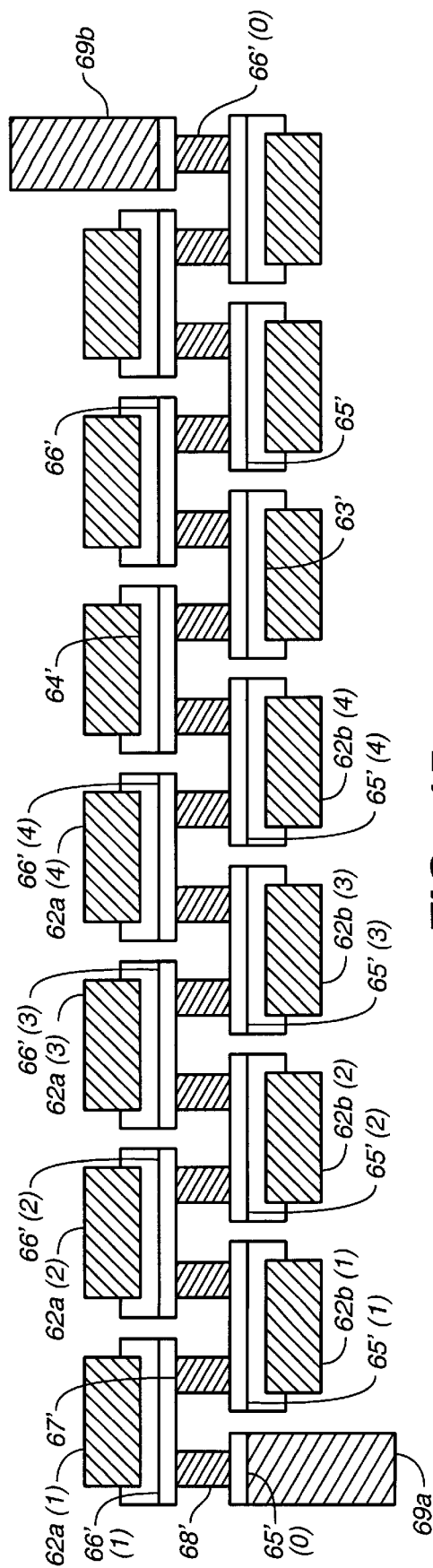
FIG._15

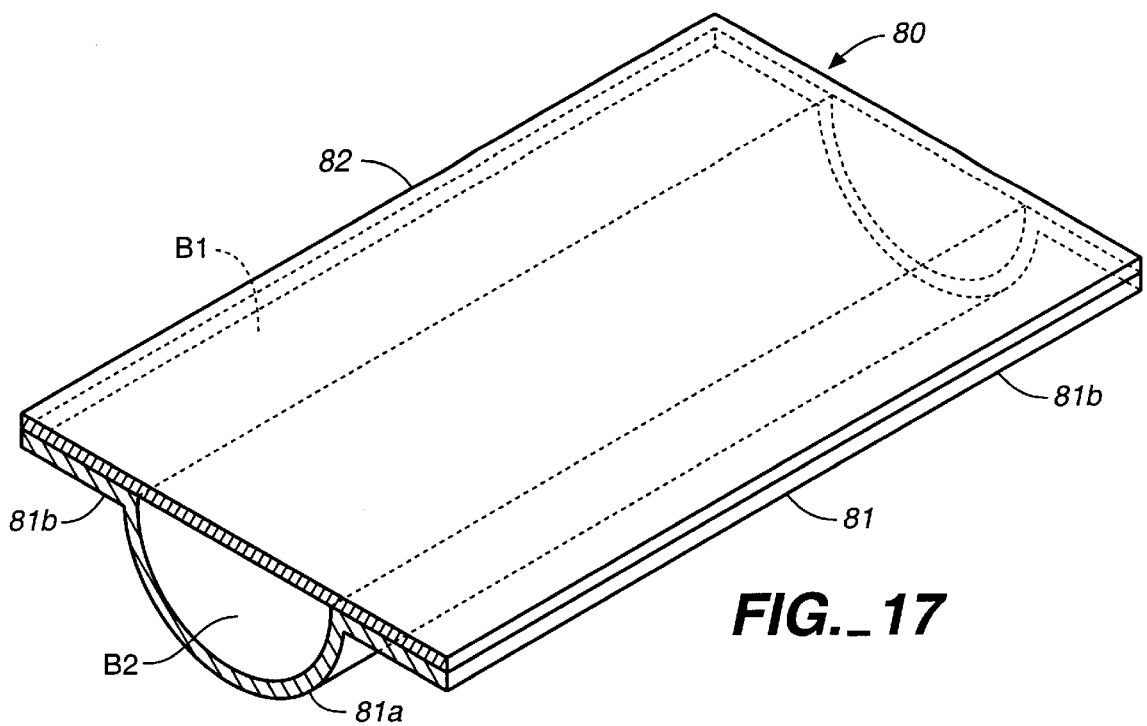
FIG._17
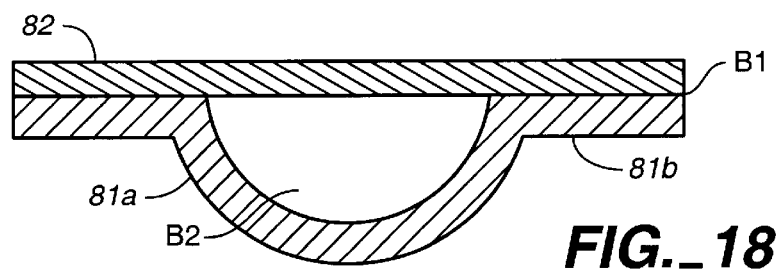
FIG._18
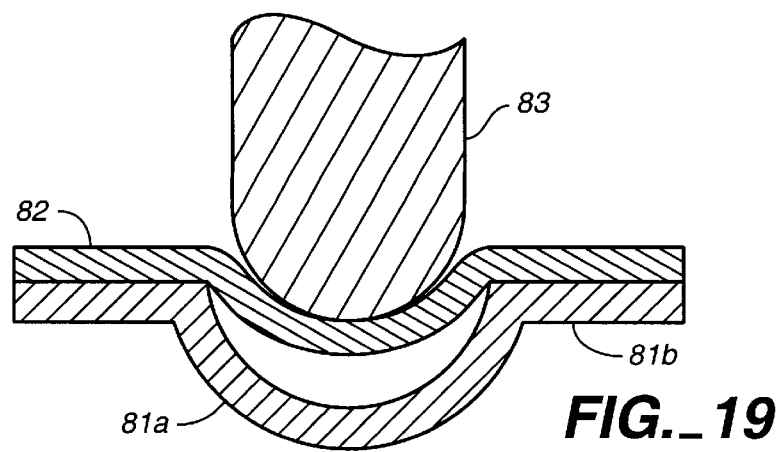
FIG._19

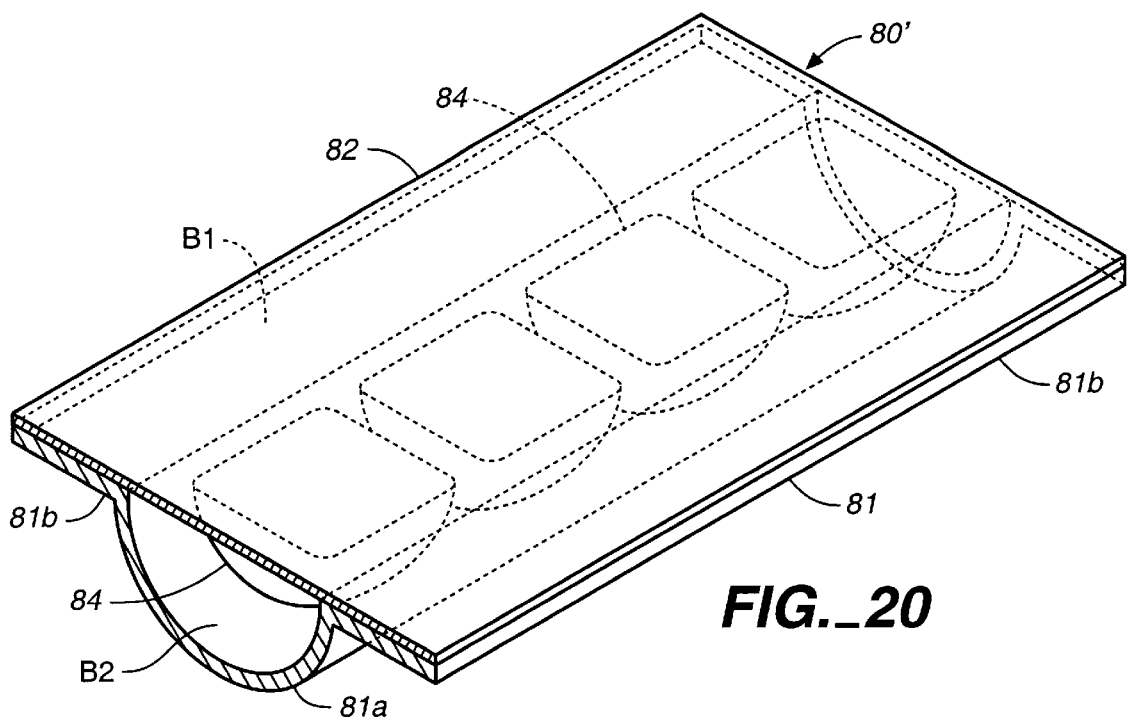
FIG._20
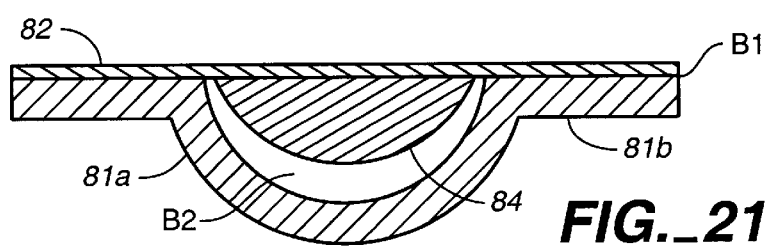
FIG._21
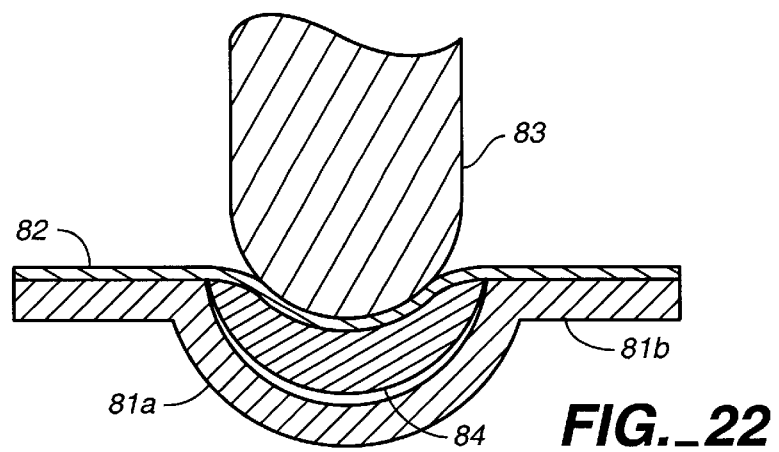
FIG._22

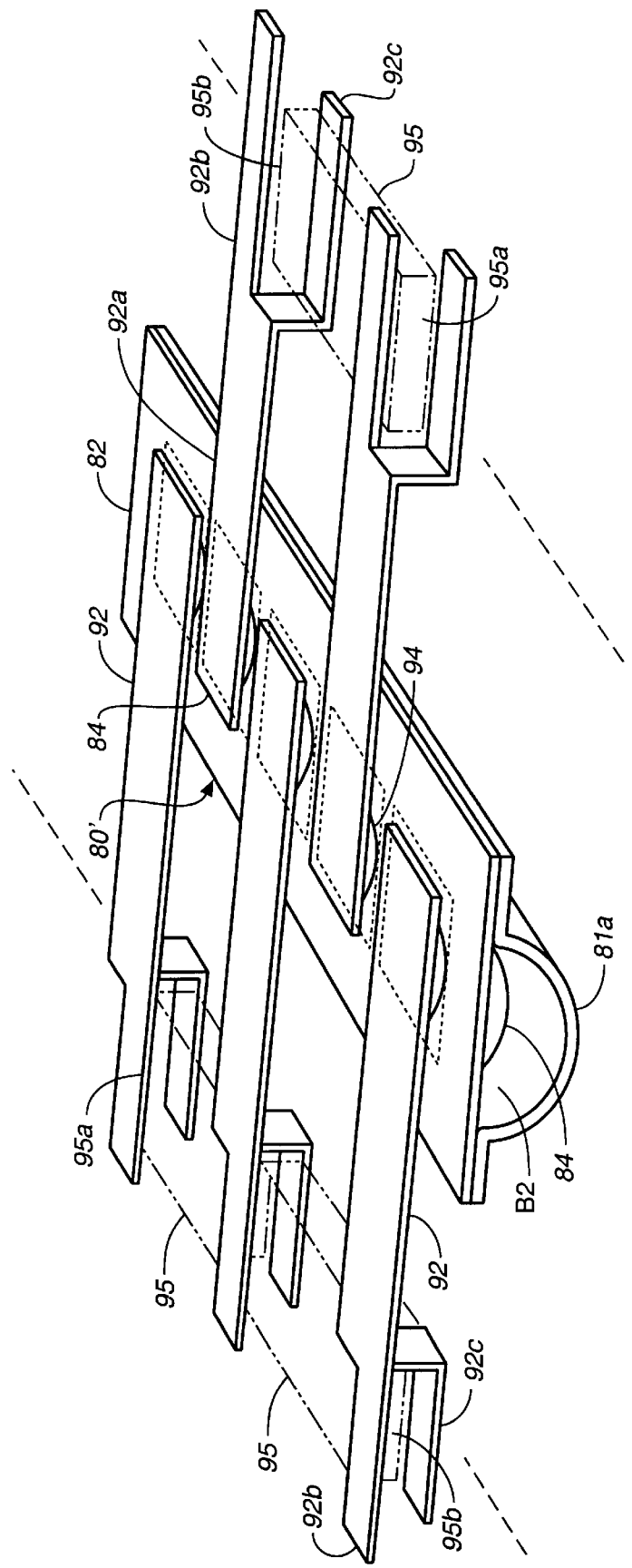
FIG._23

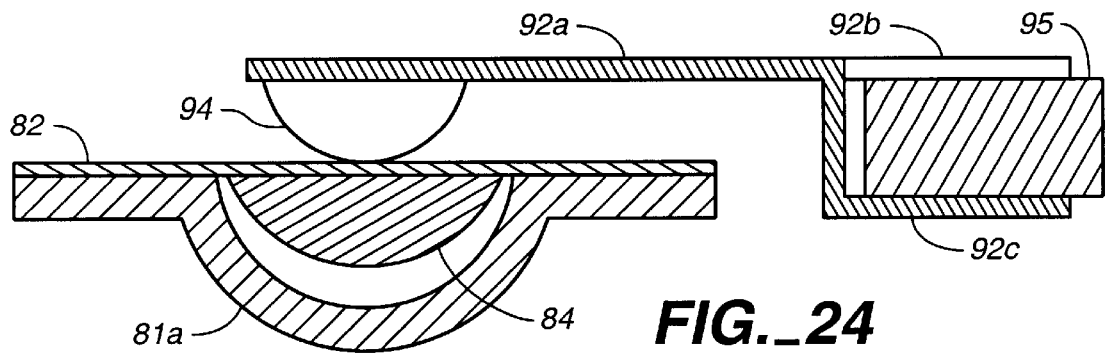
FIG._24
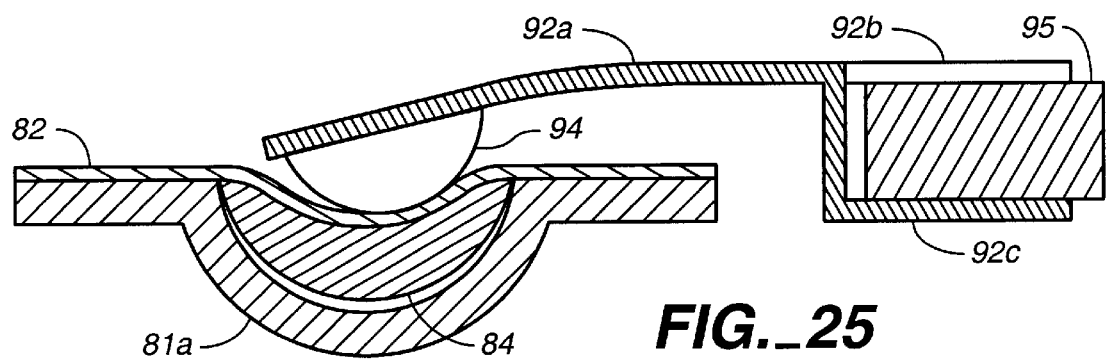
FIG._25
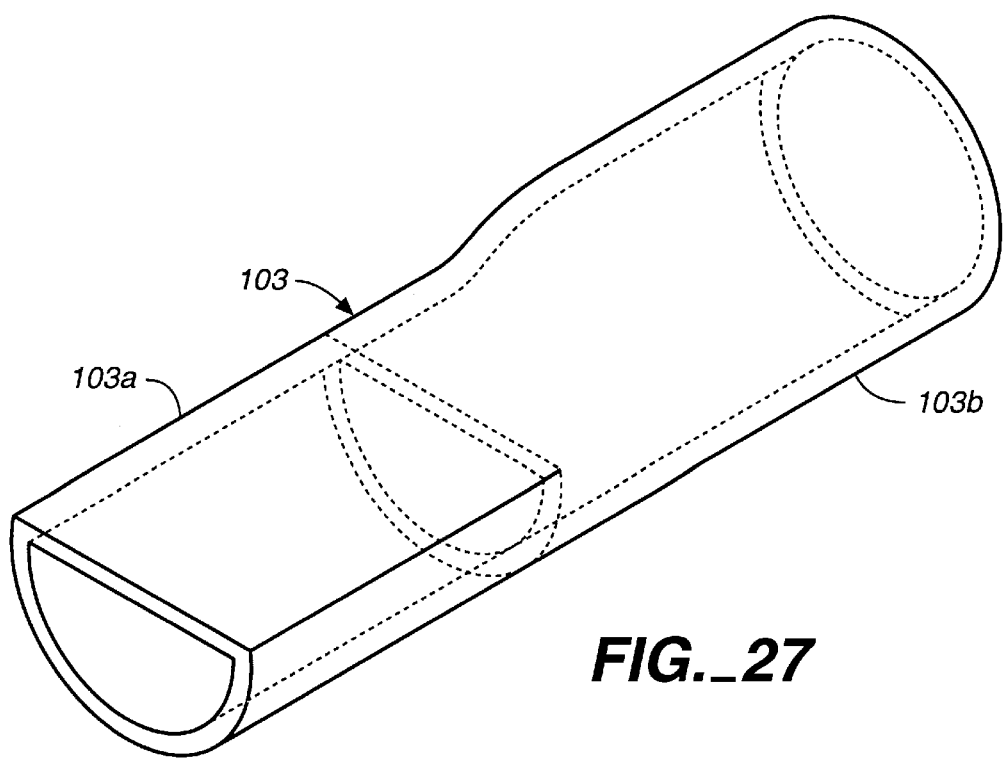
FIG._27

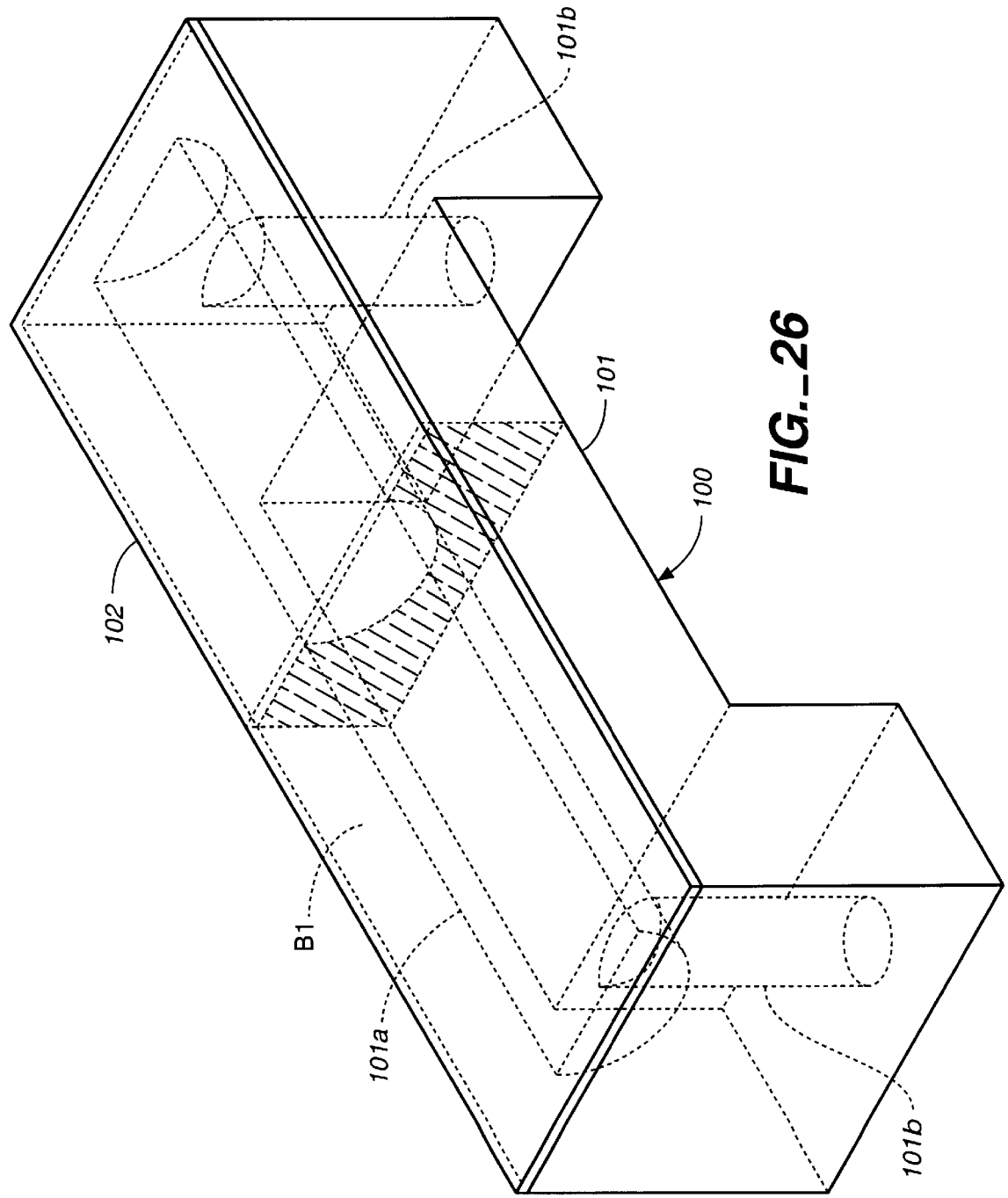
FIG._26

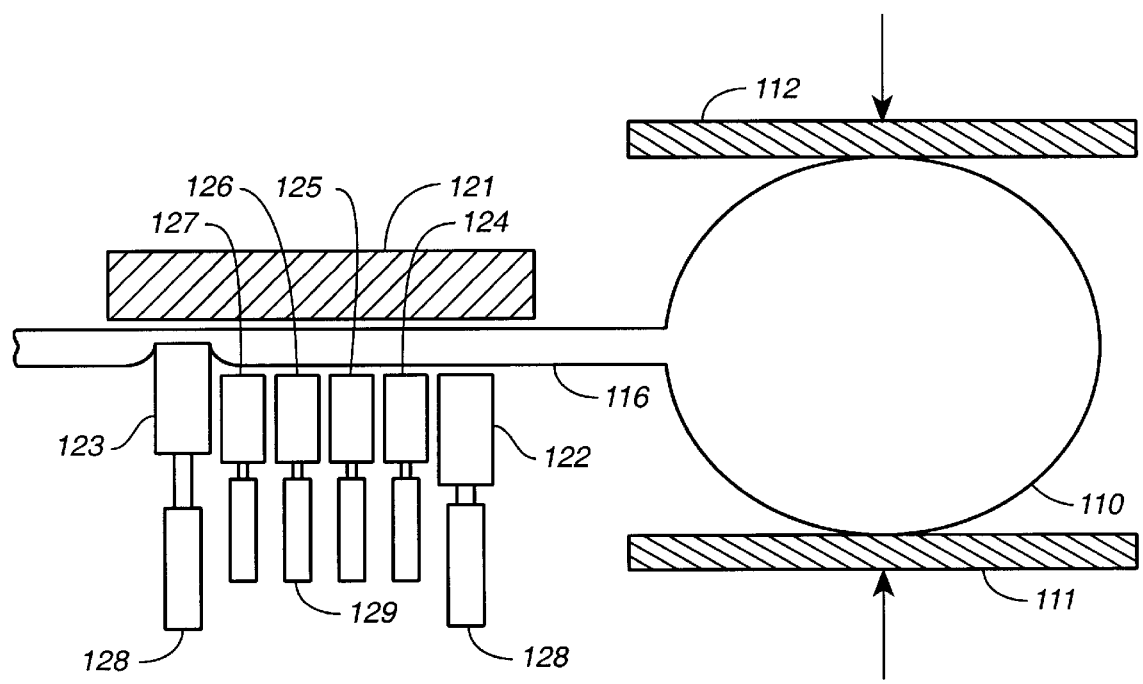
FIG._28
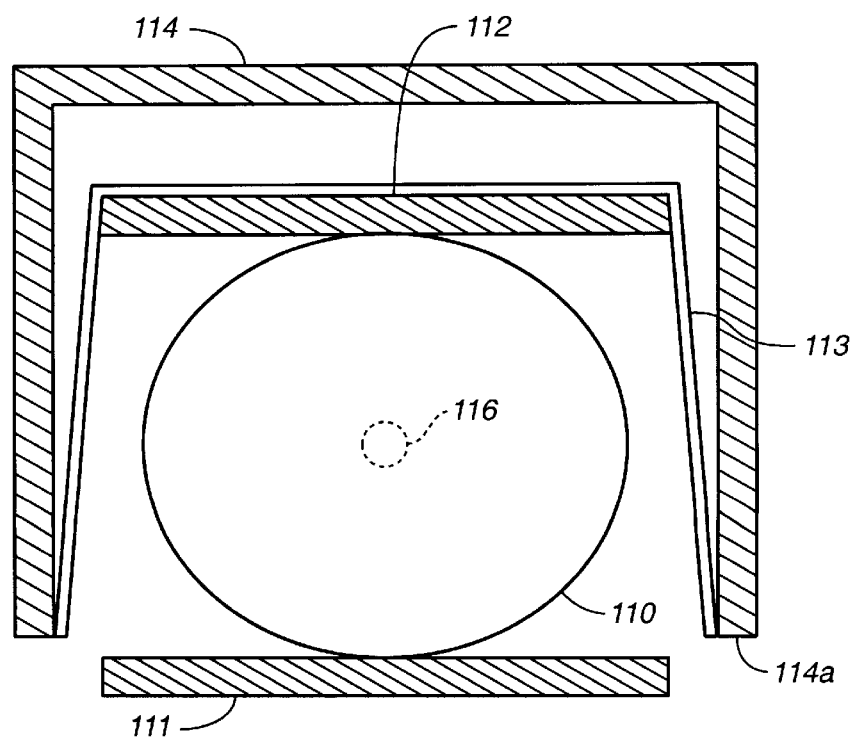
FIG._29

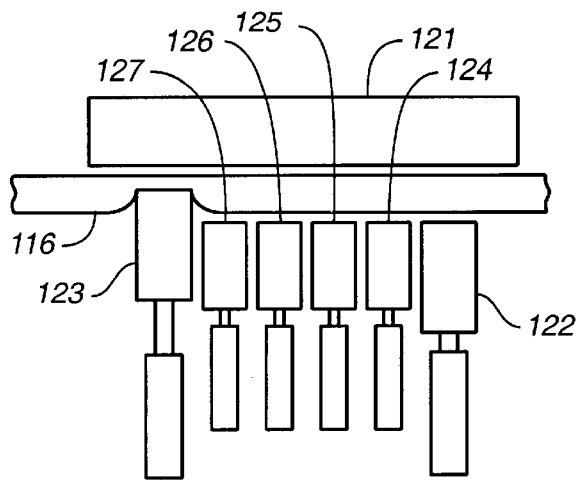
FIG._30
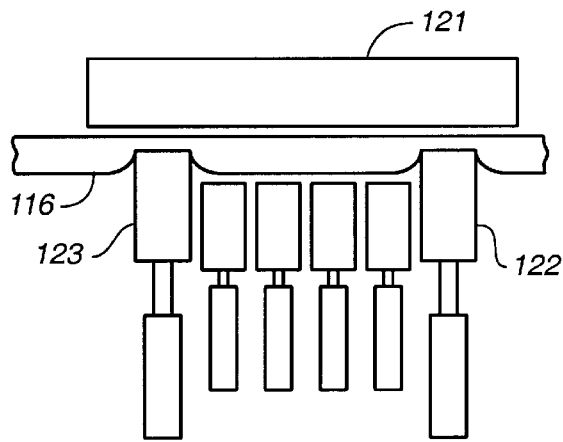
FIG._31
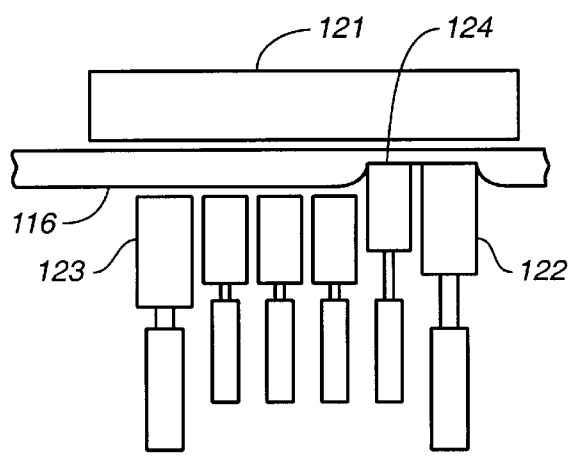
FIG._32
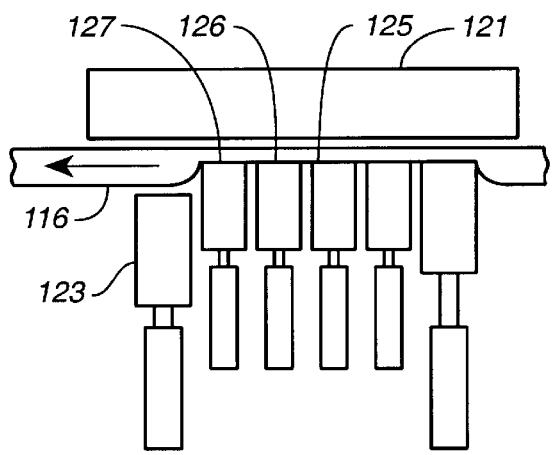
FIG._33

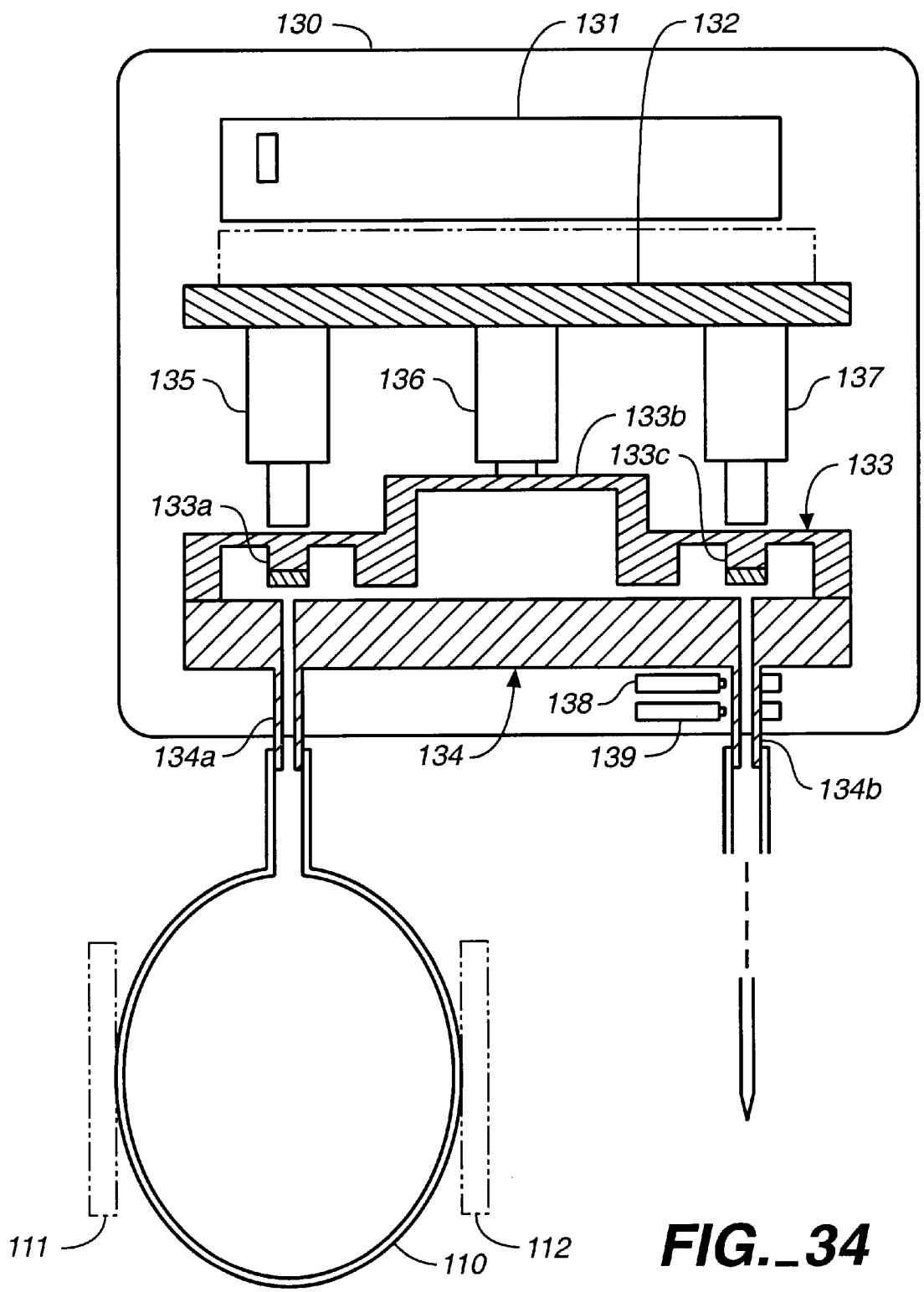
FIG._34

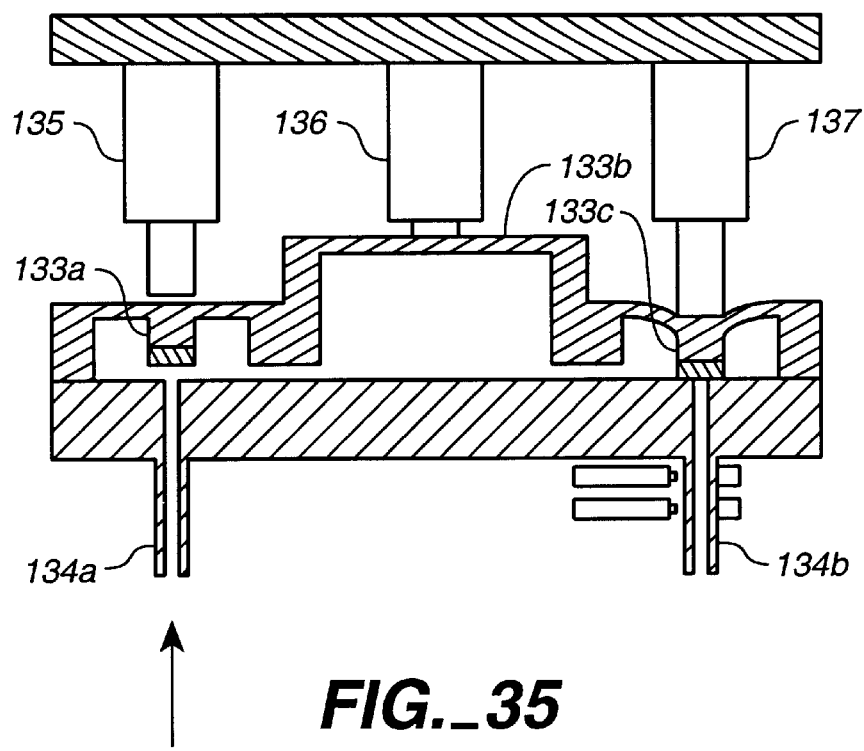
FIG. _35
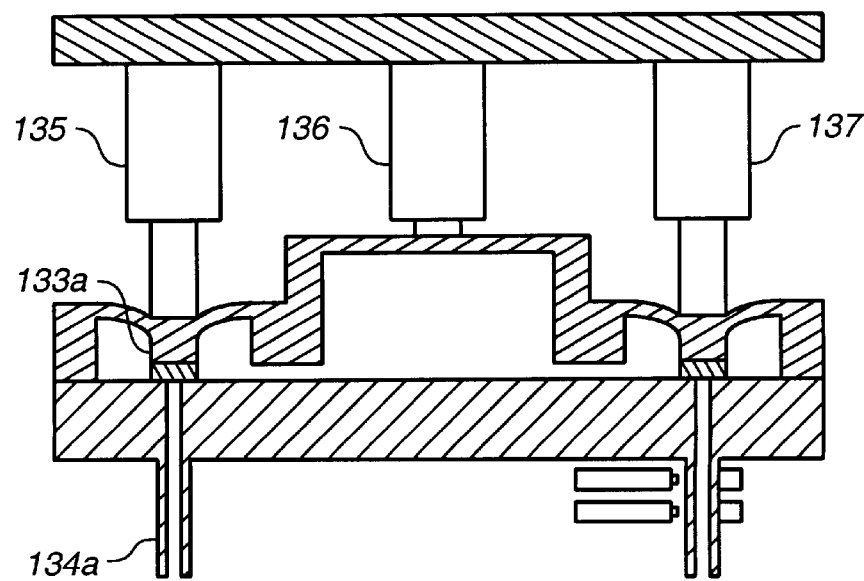
FIG. _36

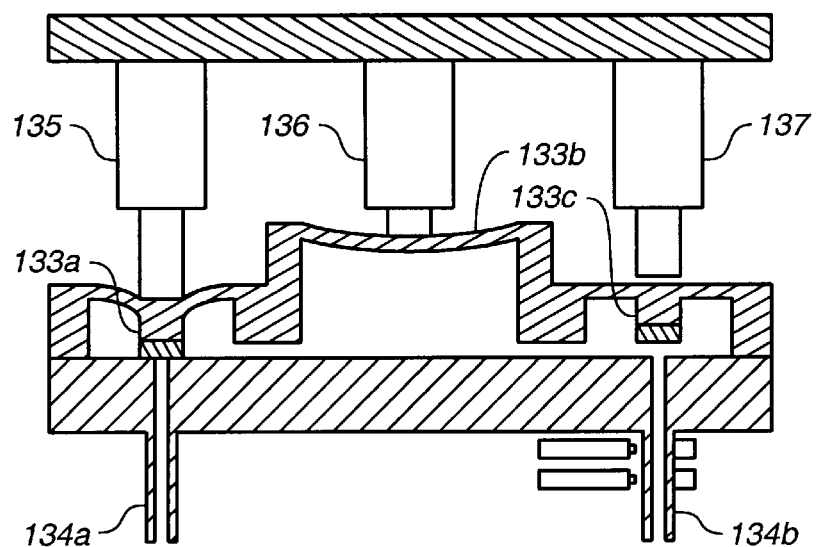
FIG._37
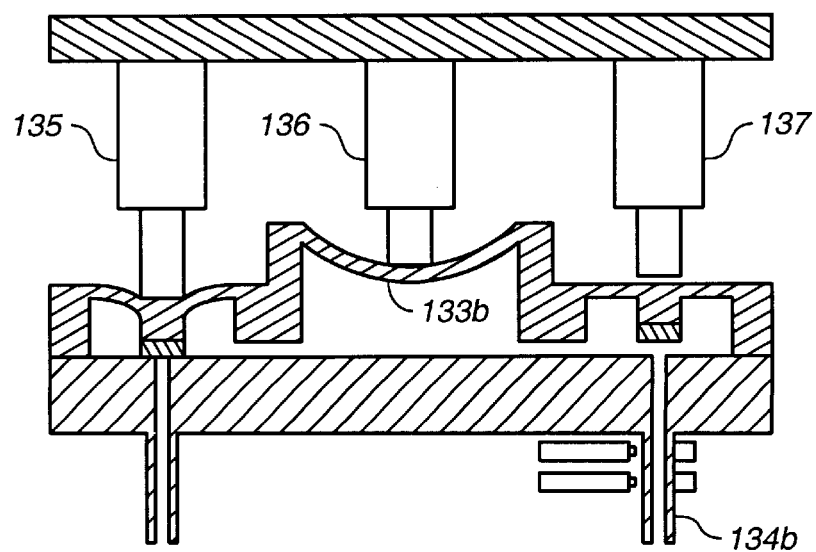
FIG._38

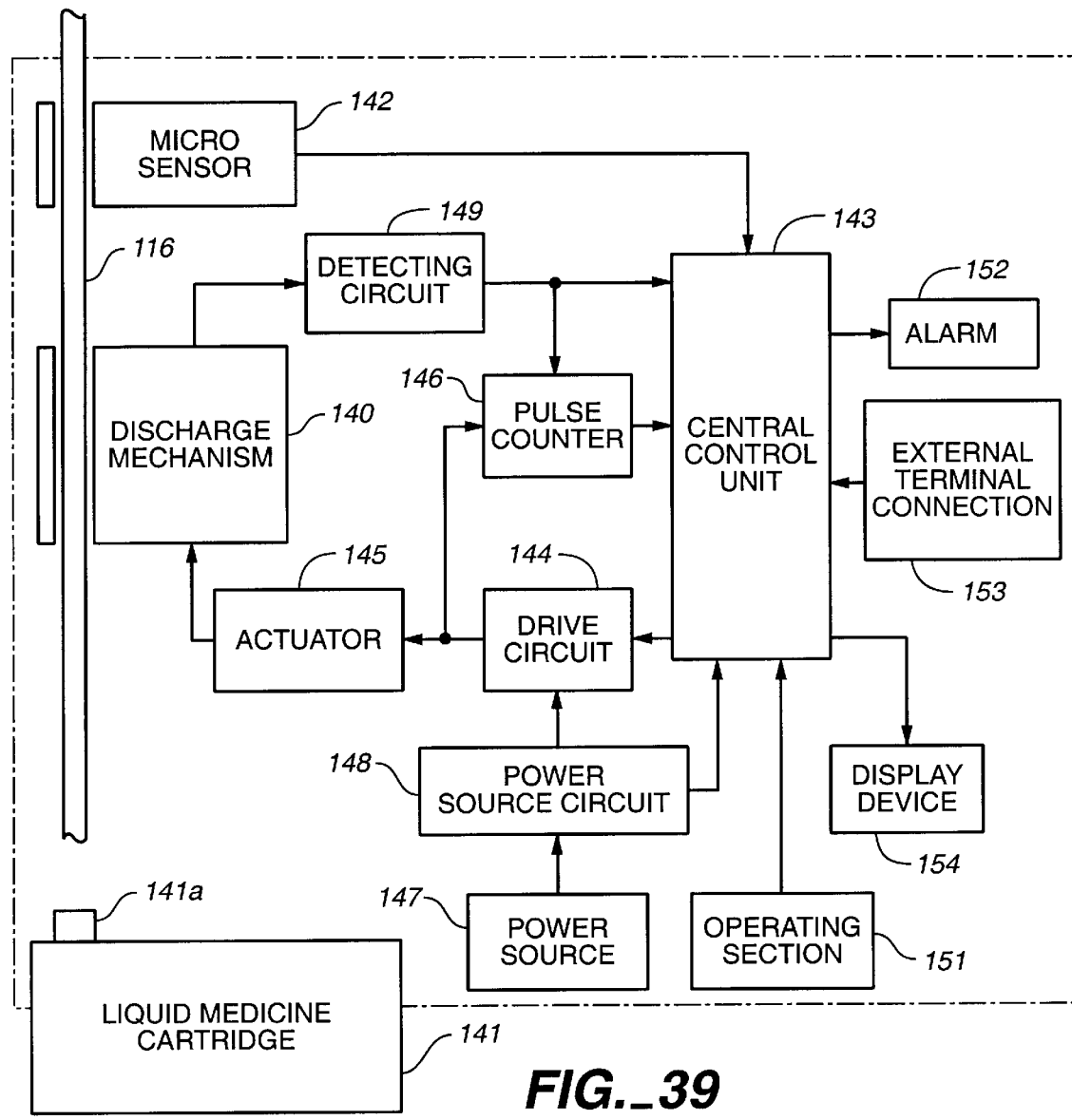
FIG._39

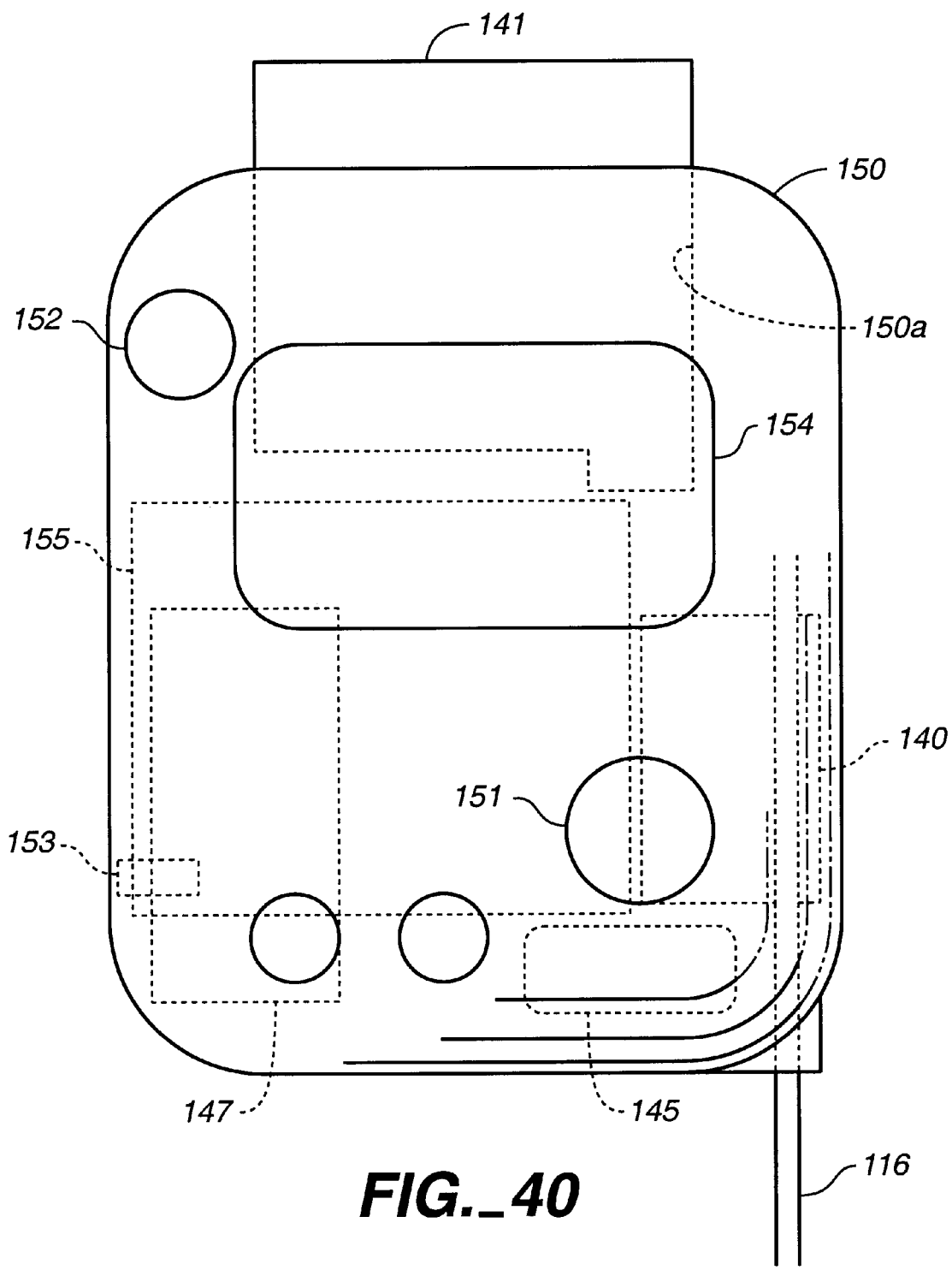
FIG._40

TRANSFUSION DEVICE AND LIQUID SUPPLY TUBE

BACKGROUND OF THE INVENTION

1. Technical Field

The present invention relates to a transfusing device and a liquid supply tube and, in particular, to a structure suitable for a transfusing device for injecting a liquid medicine into the body of a patient and to a structure suitable for a liquid supply tube, which is a constituent part of a transfusing device.

2. Background Art

In a hospital or the like, a liquid medicine is injected into the body of a patient usually by drip transfusion, in which a plastic transfusing tube is connected to a liquid medicine sack, which is suspended from above, and a needle is attached to the forward end of the transfusing tube and inserted into a blood vessel of the patient or the like. To accurately control the amount of liquid medicine or to enhance the safety of the operation, various types of transfusing device constructed so as to be capable of forcibly sending the liquid medicine into the body of the patient may be adopted.

In one type of such transfusing device, a peristaltic transfusing pump may be employed in which the liquid medicine in a flexible liquid supply tube is conveyed by squeezing the liquid supply tube. Two types of peristaltic transfusing pump are employed: one is a rotary type transfusing pump in which a flexible liquid supply tube is bent into a semi-circular shape and in which the bent portion of the liquid supply tube is squeezed from inside to conveyed liquid medicine by a roller mounted to the forward end of a rotatable arm provided on the inner side of the bent portion of the liquid supply tube; and the other is a finger type transfusing pump in which a plurality of fingers (pressurizing members) are sequentially pressed against the outer surface of the liquid supply tube in the direction in which the liquid medicine in the liquid supply tube is to be conveyed to thereby convey the liquid medicine.

The rotary type transfusing pump is advantageous in that it has a relatively simple structure. However, it is relatively difficult to accurately control the minute amount of liquid medicine to be conveyed. Further, it does not easily allow the size of the conveying section to be reduced.

A typical example of the finger type transfusing pump is disclosed in Japanese Patent Publication No. 61-55393. In the transfusing pump of the above example, a finger is engaged with each of a plurality of cam plates mounted to a rotation shaft, and the fingers are caused to move toward and away from the liquid supply tube by rotating operation of the cam plates when the rotation shaft rotates. This peristaltic transfusing pump using fingers is advantageous in that the injection pressure for the liquid medicine can be made high and that the minute amount of liquid medicine can be controlled with high accuracy. However, since it is necessary to drive a large number of fingers with high accuracy, the structure of the pump is rather complicated, making it difficult to reduce the production cost. Further, it is difficult to achieve a reduction in size.

A balloon type transfusing device provides a function equivalent to that of the above transfusing device. In the balloon type transfusing device, liquid medicine is put in the balloon, which is formed of synthetic rubber or the like, in advance, and the liquid medicine is pushed forward by contraction force of the balloon. This transfusing device is advantageous in that it has a very simple structure and can be produced at low cost. However, in a transfusing device using a balloon, the discharge pressure of the liquid medicine varies depending upon the amount of liquid medicine left in the balloon, so that the speed at which the liquid medicine is supplied also varies. More specifically, the discharge pressure is gradually reduced from the initial pressure as the transfusion time elapses, and the amount of liquid medicine supplied also diminishes gradually. In this way, the supply pressure for the liquid medicine and its amount supplied vary. Further, it is difficult to control the speed at which the liquid medicine is supplied.

In performing medical treatment, it is sometimes necessary to give a minute amount of liquid medicine over a long period of time to mitigate the strain on the patient. To make it possible to give liquid medicine over a long period of time, development of a portable transfusing device is to be expected. To realize a portable transfusing device, a reduction in the size and weight of the device is indispensable. Conventionally, there has been proposed no transfusing device structure which is small and light enough to provide a satisfactory portability. Further, it is not yet technically possible to administer a minute amount of liquid medicine into the body of the patient with high accuracy.

DISCLOSURE OF INVENTION

In a first aspect of the present invention, there is provided a transfusing device comprising a flexible liquid supply tube, a support member supporting the liquid supply tube from one side, and a rotary drive member which is adjacent to the liquid supply tube on the opposite side of the support member and which is equipped with a rotation shaft substantially parallel with the direction in which the liquid supply tube extends, wherein one or a plurality of pressing protrusions for pressurizing the liquid supply tube are integrally provided on the outer peripheral surface of the rotary drive member, and wherein the pressing protrusions are spirally formed or spirally arranged on the outer peripheral surface of the rotary drive member.

In a second aspect of the present invention, there is provided a transfusing device comprising a flexible liquid supply tube, a support member supporting the liquid supply tube from one side, and a plurality of fingers which are adjacent to the liquid supply tube on the opposite side of the support member and which are arranged substantially parallel with the direction in which the liquid supply tube extends, wherein the fingers act on the liquid supply tube to pressurize the liquid supply tube, wherein there is provided a heat transfer means for heating or cooling the fingers or a drive member for driving the fingers, and wherein the fingers or the drive member is formed of a heat deformation material which deforms so as to pressurize the liquid supply tube by the heat transfer of the heat transfer means.

In a third aspect of the present invention, there is provided a liquid supply tube which deforms by external stress due to at least partial flexibility and which conveys liquid medicine therein by this deformation, wherein there are provided a pair of component members at least one of which is equipped with a plate like portion formed of an elastic material or a flexible material, and wherein the two sides with respect to the width direction of the component members are joined together to form joint portions, the gap defined between the joint portions being formed as a liquid passage.

In a fourth aspect of the present invention, there is provided a transfusing device comprising liquid pressurizing means for pressurizing liquid medicine, a flexible liquid supply tube connected to the liquid pressurizing means, a support member supporting the liquid supply tube from one side, a first finger which is adjacent to the liquid supply tube on the opposite side of the support member, which is arranged substantially parallel with the direction in which the liquid supply tube extends and which is arranged at the upstream end, a second finger arranged at the downstream end, and a plurality of third fingers arranged between the first finger and the second finger, the liquid supply tube being capable of causing the first, second and third fingers to act on the liquid supply tube to pressurize them, wherein the liquid medicine is discharged by sequentially repeating the following steps: a step for pressurizing the liquid supply tube by the first finger with the second finger pressurizing the liquid supply tube, a step for canceling the pressurization by the second finger and pressurizing the liquid supply tube by the third fingers, and a step for pressurizing the liquid supply tube by the second finger to cancel the pressurization by the first finger and canceling the pressurization by the third fingers.

In a fifth aspect of the present invention, there is provided a transfusing device comprising liquid pressurizing means for pressurizing liquid medicine, a transfusion route for conveying the pressurized liquid medicine, and a transfusion pump provided in the transfusion route, wherein the transfusion pump is equipped with an inlet valve provided at the inlet of the pump, a pump chamber formed on the inner side of the introducing valve, a discharge valve provided at the outlet of the pump, and a discharge mechanism for discharging the liquid medicine by varying the volume of the pump chamber, and wherein the liquid medicine is discharged by sequentially repeating the following steps: a step for closing the inlet valve with the discharge valve being closed, a step for opening the discharge valve and effecting a reduction in the volume of the pump chamber by the discharge mechanism, and a step for closing the discharge valve and opening the inlet vale to restore the volume of the pump chamber.

In all of the above aspects of the invention, a reduction in the size and weight of the device can be achieved as compared with the conventional transfusing devices by reducing the number of parts, simplifying the structure of the device, etc. Further, in all of them, it is possible to supply a minute amount of liquid medicine with high accuracy.

In the above aspects of the invention, the liquid supply tube is a flexible tube which is deformed in order to send out the liquid medicine therein in the direction in which the tube extends. It is formed, for example, by synthetic resin and arranged in the transfusing device. The transfusing tube as described in the present specification is a tube for supplying the liquid medicine conveyed from the transfusing device to the patient. Usually, it is equivalent to what is connected to the liquid medicine sack used in transfusion. Although it is desirable for the liquid supply tube to be formed of a special material which has enough durability to withstand repeated deformation, it may also be formed of a material similar to that of the transfusing tube. Alternatively, a part of the transfusing tube may be used as the liquid supply tube.

BRIEF DESCRIPTION OF THE DRAWINGS

FIG. 1 is a front view partly in section showing an essential part of a first embodiment in the first aspect of the present invention;

FIG. 2 is a cross-sectional view showing the essential part of the first embodiment in the first aspect of the present invention;

FIG. 3 is a front view partly in section showing the essential part of the first embodiment in the first aspect of the present invention in a different state;

FIG. 4 is a front view partly in section showing an essential part of a second embodiment in the first aspect of the present invention;

FIG. 5 is a plan view of a rotary drive member of the second embodiment in the first aspect of the present invention;

FIG. 6 is a cross-sectional view showing an essential part of a third embodiment in the first aspect of the present invention;

FIG. 7 is a cross-sectional view showing an essential part of a fourth embodiment in the first aspect of the present invention;

FIG. 8 is a plan view showing the configuration of an insertion plate of the fourth embodiment in the first aspect of the present invention;

FIG. 9 is a front view showing the inner structure of a first embodiment in the second aspect of the present invention;

FIG. 10 is a left-hand side front view showing the inner structure of the first embodiment in the second aspect of the present invention;

FIG. 11 is an enlarged sectional view showing the sectional configuration of a heat generating portion of a thermal array of the first embodiment in the second aspect of the present invention;

FIG. 12 is a schematic perspective view showing an essential part of a second embodiment in the second aspect of the present invention;

FIG. 13 is a schematic longitudinal sectional view showing an essential part of a third embodiment in the second aspect of the present invention;

FIG. 14 is a schematic longitudinal sectional view showing an essential part of a fourth embodiment in the second aspect of the present invention;

FIG. 15 is a schematic longitudinal sectional view taken along a plane orthogonal to the section of FIG. 14, showing the essential part of the fourth embodiment in the second aspect of the present invention;

FIG. 16 is a schematic enlarged plan view showing the structure and arrangement of fingers of the fourth embodiment in the second aspect of the present invention;

FIG. 17 is a partial perspective view schematically showing the structure of a liquid supply tube of a first embodiment in the third aspect of the present invention;

FIG. 18 is a longitudinal sectional view showing the sectional structure of the first embodiment in the third aspect of the present invention;

FIG. 19 is a longitudinal sectional view showing a modification of the first embodiment in the third aspect of the present invention;

FIG. 20 is a partial perspective view schematically showing the structure of a liquid supply tube of a second embodiment in the third aspect of the present invention;

FIG. 21 is a longitudinal sectional view showing the sectional structure of the second embodiment in the third aspect of the present invention;

FIG. 22 is a longitudinal sectional view showing a modification of the second embodiment in the third aspect of the present invention;

FIG. 23 is a schematic perspective view showing the structure of a transfusing pump according to the second embodiment in the third aspect of the present invention;

FIG. 24 is a longitudinal sectional view showing the sectional configuration of a transfusing pump according to the second embodiment in the third aspect of the present invention;

FIG. 25 is a longitudinal sectional view showing a modification of the transfusing pump according to the second embodiment in the third aspect of the present invention;

FIG. 26 is a schematic perspective view showing the structure of a third embodiment in the third aspect of the present invention;

FIG. 27 is a schematic perspective view showing the configuration of a connection connector for connecting the first or the second embodiment in the third aspect of the present invention to the transfusing tube;

FIG. 28 is a schematic diagram showing the structure of an embodiment in the fourth aspect of the present invention;

FIG. 29 is a liquid medicine pressurizing structure according to an embodiment in the fourth aspect of the present invention;

FIGS. 30 through 33 are schematic diagrams showing how a transfusing pump according to an embodiment in the fourth aspect of the invention operates;

FIG. 34 is a schematic diagram showing the structure of an embodiment in the fifth aspect of the present invention;

FIGS. 35 through 38 are schematic diagrams showing how a transfusing pump according to an embodiment in the fifth aspect of the invention operates;

FIG. 39 is a schematic diagram showing the general construction of a transfusing device that can be commonly used in the embodiments in the first, second, fourth and fifth aspects of the present invention; and FIG. 40 is a schematic front view showing the appearance of a transfusing device that can be commonly used in the embodiments in the first, second, fourth and fifth aspects of the present invention.

BEST MODE FOR CARRYING OUT THE INVENTION

To describe the present invention more specifically, a plurality of preferable embodiments will be described with reference to the accompanying drawings.

EMBODIMENTS IN THE FIRST ASPECT OF THE INVENTION

In the first aspect of the present invention, there is provided a pressing protrusion spirally formed on the outer peripheral surface of a rotary drive member or a plurality of spirally arranged pressing protrusions; by rotating the rotary drive member, that portion of the liquid supply tube pressed by the pressing protrusion is moved to thereby convey the liquid medicine.

First Embodiment

FIG. 1 is a front view showing the essential part of a transfusing device according to the first embodiment of the present invention, and FIG. 2 is a cross-sectional view showing the essential part of the transfusing device of the first embodiment. In this transfusing device, a support plate 22 is mounted on a base 10 through the intermediation of springs 11. At a position opposite to this support plate 22, a cylindrical rotary drive member 24 equipped with a rotation shaft 23 is rotatably arranged. While this rotation shaft 23 is formed integrally with the rotary drive member 24, it is possible, in a modification, for the rotation shaft 23 and the rotary drive member 24 to be formed as separate members and firmly attached to each other by adhesion, welding or the like. A liquid supply tube 16 is arranged between the support plate 22 and the rotary drive member 24. The axis of the rotation shaft 23 and the rotary drive member 24 is parallel with the direction in which the liquid supply tube 16 extends (i.e., vertically as seen in the drawing).

On the outer peripheral surface of the rotary drive member 24, a pressing protrusion 24a extending spirally around the axis thereof is formed integrally. This pressing protrusion 24a pressurizes the liquid supply tube 16 through the intermediation of a sheet 25 described below and depresses the flexible liquid supply tube 16. When the rotation shaft 23 is rotated by a drive motor (not shown) or the like, the pressing protrusion 24a on the outer peripheral surface of the rotary drive member 24 also rotates. As a result, that portion of the liquid supply tube 16 which is depressed by the pressing protrusion 24a is gradually displaced downwards.

A cylindrical flexible sheet 25 is fitted onto the rotary drive member 24 and exists between the liquid supply tube 16 and the rotary drive member 24. The upper and lower ends of this sheet 25 is fastened directly or indirectly to the base 10 and the support plate 22. The sheet 25 serves to restrain the generation of twisting, etc. of the liquid supply tube 16 when it receives frictional stress in the rotating direction as a result of the pressing protrusion 24a of the rotary drive member 24 coming into direct contact with the liquid supply tube 16. It is desirable that at least the surface of that side which comes into contact with the rotary drive member 24 offer low friction.

In order that no stress in an undesirable direction may be generated in the liquid supply tube 16 as stated above, it is most desirable for the sheet 25 to be directly or indirectly fastened to the base 10 and the support plate 22. Conversely, it may be directly or indirectly fastened to the rotation shaft 23 and the rotary drive member 24. In this case, it is desirable for the surface of that side of the sheet 25 which comes into contact with the liquid supply tube 16 of the sheet 25 to have low friction. To mitigate the frictional force on the surface of the sheet, it is possible to form the sheet of a material offering little friction, or provide a low friction coating on the surface of the sheet.

As shown in FIG. 2, the support plate 22 has an opposing surface 22a which has an arcuate sectional configuration such that it wraps up the rotary drive member 24 from the right-hand side as seen in the drawing. The liquid supply tube 16 is held between this opposing surface 22a and the sheet 25 surrounding the surface of the rotary drive member 24.

When the rotary drive member 24 rotates, the spiral pressing protrusion 24a formed on the outer peripheral surface thereof also rotates, and that portion of the pressing protrusion 24a which depresses the liquid supply tube 16 is gradually displaced downwards. When this depressing portion has moved to the lower end of the support plate 22, the pressing protrusion 24a starts to depress the liquid supply tube 16 in the vicinity of the upper end of the support plate 22, as shown in FIG. 3, and this depressing portion moves again downwards from the upper end of the support plate 22. This downward displacement (peristaltic motion) of the depressing portion is repeated, and the liquid medicine in the liquid supply tube 16 continues to be conveyed downwards as seen in the drawing.

In this embodiment, the vertical length of the support plate 22 and the pitch of the pressing protrusion 24a are substantially the same, and there is always a depressed portion which is being depressed by the pressing protrusion 24a within the area in which the liquid supply tube 16 is in contact with the support plate 16. The pitch of the spiral pressing protrusion 24a is not larger than the vertical length of the support plate 22, and within a range not less than the least diameter that allows deformation corresponding to the flexibility of the liquid supply tube 16 and the sheet 25. It is possible to make the spiral pitch of the pressing protrusion 24a smaller so that the liquid supply tube 16 may be depressed at a plurality of positions. If the spiral pitch of the pressing protrusion 22 is larger than the vertical length of the support plate 22, it is possible to convey the liquid medicine although in that case there is a possibility of an uncontrolled flow of liquid medicine being generated. There is practically no problem if the spiral pitch is slightly larger than the length of the support plate 22. When, conversely, the pitch is less than the least diameter that allows deformation of the liquid supply tube 16 and the sheet 25, the pump capacity of the transfusion pump is lost, or the pumping efficiency thereof deteriorates.

In this embodiment, pumping operation is possible solely by attaching the rotary drive member 24 to the rotation shaft 23 and rotating them. Thus, there is no need to provide as in the case of the conventional finger type transfusion pump to provide an assembly formed by a large number of cam plates and depression fingers, so that it is possible to achieve a reliable liquid supply function with a very simple structure. Thus, due to the simple structure, a reduction in size is possible, and the number of parts is reduced. At the same time, a reduction in cost is achieved due to the improvement in assembly. Further, since failure occurs less often, an improvement is achieved in terms of safety and maintenance.

In particular, in this embodiment, a spiral pressing protrusion is provided on the outer peripheral surface of the rotary drive member, whereby, unlike the case of the conventional finger type transfusion pump, it is possible to squeeze the liquid supply tube endlessly and continuously (move the depressing portion in the direction in which it extends), so that it is possible to eliminate vibration of the support plate 12 pressurized by the springs 11, convey the liquid medicine efficiently, and improve the pumping efficiency. Further, it is possible to restrain pulsation of the liquid medicine.

In this embodiment, it is also possible to simultaneously adopt various improved systems of the conventional finger type transfusion pumps. For example, to reduce the supply pressure of the liquid medicine due to the operating period of the transfusion pump or pulsation of the supply speed, it is possible to arrange depression fingers which come in and out so as to vary the liquid passage sectional area of the liquid supply tube 16 in synchronism with the pulsation period of the liquid medicine. These fingers operate so as to compensate for the pulsation of the liquid medicine, so that it is possible to mitigate the pulsation and create a constant liquid medicine flow. Further, to provide a function by which stopping of the liquid medicine in the liquid supply tube is detected to give alarm, it is possible to provide a mechanism for detecting the difference between the inner pressure on the upstream side and the inner pressure on the downstream side, that is, difference in pressure between the inlet and outlet of the pump.

Second Embodiment

Next, a second embodiment of the present invention will be described with reference to FIGS. 4 and 5. Like the first embodiment, this embodiment is equipped with the base 10, the springs 11, the support plate 22, the rotation shaft 23 and the sheet 25. It differs from the first embodiment in that a rotary drive member 34 is provided instead of the rotary drive member 24. This rotary drive member 34 is fastened to the rotation shaft 23 and equipped with a plurality of disc-like drive sections 34a which are decentered with respect to the rotation axis. As shown in FIG. 5, this rotary drive member 34 consists of a plurality of drive sections 34a of the same configuration which are sequentially deviated from each other by 45 degrees around the axis of the rotation shaft 23.

This rotary drive member may be cut from a solid shaft material by a machine tool capable of micro three-dimensional machining. Alternatively, each drive section 34a may be formed by cutting, stamping, forging, etc., and then the drive sections 34a may be formed into an integral unit in which the phase difference θ between adjacent drive sections 34a (See FIG. 5) is 45 degrees by adhesion, crimping, welding, etc. Further, it is not necessary for the drive sections 34a to be directly fastened to each other. They may be indirectly formed into an integral unit by being individually fastened to the rotation shaft 23.

In this embodiment, each decentered drive section 34a may have a circular plan configuration. Alternatively, it may be a deformed circular configuration. Further, instead of being decentered, all the drive sections may be arranged concentrically. In this case, protrusions protruding simply from the outer peripheral surface are provided, and the angular positions of the protrusions are deviated from each other. In any case, in each drive section 34a, a pressing protrusion 34b that is most protruding from the axis of the rotation shaft 23 is formed in any one section of the outer peripheral surface. In the drive section adjacent to this pressing protrusion 34b, deviation by the phase difference (45 degrees) is effected, whereby a plurality of pressing protrusions 34b are arranged on the outer peripheral surface of the rotary drive member 34 spirally as a whole at intervals corresponding to the above phase difference.

While in this embodiment the phase difference θ between adjacent drive sections is 45 degrees, it may, for example, be a value corresponding to a divisor corresponding to a rotation angle, such as 20 degrees, 30 degrees, 36 degrees, 60 degrees, etc.

Third Embodiment

Next, a third embodiment of the present invention will be described with reference to FIG. 6. In this embodiment, the structures of the rotation shaft 23 and the rotary drive member 24 are completely the same as those of the first embodiment. This embodiment differs from the first embodiment in that a flexible sheet 28 surrounds the liquid supply tube 16. End portions of the sheet 28, which surrounds the liquid supply tube 16, are attached to a support plate 26 by a fastening member 27. The position at which the sheet 28 is fastened to the support plate 26 is in a direction along the rotation tangent on the liquid supply tube 16 side of the rotary drive member 24 and deviated to a direction opposite to the direction in which the rotary drive member 24 rotates as seen from the liquid supply tube 16 (the liquid supply tube 16 being used as a reference).

In this embodiment, the sheet 28 substantially surrounds the liquid supply tube 16, and is fastened on the side opposite to the liquid supply tube 16 is moved by its frictional force as the rotary drive member 24 rotates, and the liquid supply tube 16 is held by the sheet 28 so that it may not move in the rotating direction of the rotary drive member 24, so that twisting, etc. of the liquid supply tube 16 is not easily generated if there is frictional force between the sheet 28 and the rotary drive member 24.

The construction of this embodiment regarding the sheet 28 can also be applied to the case in which the rotary drive member 34 of the second embodiment is used.

Fourth Embodiment

FIGS. 7 and 8 show the structure of a fourth embodiment of the present invention. In this embodiment, a comb-like partition 38 formed of a thin metal material is provided between the rotation shaft 23 and the rotary drive member 24, formed in the same manner as in the first embodiment, and the liquid supply tube 16. This partition 38 has a plurality of slits formed and arranged in the direction in which the liquid supply tube 16 extends. Due to these slits, a plurality of strip-like lead members 38a are formed. A plurality of mounting holes 38b are formed in the base portion of the partition 38, where no slits are formed. The partition 38 is fastened to a support plate 36 by fastening members 37 passed through these mounting holes 38b.

In this embodiment, when the rotary drive member 24 rotates, the pressing protrusion 24a deforms one of the lead members 38a of the partition 38 to indirectly deform the liquid supply tube 16. By making the slits relatively deep, the lead members 38a deform independently, so that it is possible to transmit any change in the position of the contact portion of the pressing protrusion 24a to the liquid supply tube 16. The pressing protrusion 24a of the rotary drive member 24 imparts stress to the liquid supply tube 16 through the lead members 38a which do not move in the rotating direction, so that it is possible to mitigate the twisting, deflection, etc. of the liquid supply tube 16 in the rotating direction of the rotary drive member 24.

The construction of the partition 38 of this embodiment is also applicable to the second embodiment, where the rotary drive member 34 is used. Further, when the partition is formed as a sheet that is flexible enough, it is possible to form no slits therein and fasten it as an integral sheet, with its one end being at a position opposite to the rotating direction of the rotation tangential direction of the rotary drive member 24, the sheet being inserted between the rotary drive member 24 and the liquid supply tube 16.

EMBODIMENTS IN THE SECOND ASPECT OF THE PRESENT INVENTION

In the second aspect of the present invention, there is provided a transfusion pump in which the liquid supply tube is depressed by using a thermal deformation material that deforms by receiving or emitting heat.

First Embodiment

Next, a first embodiment in the second aspect of the present invention will be described with reference to the accompanying drawings. FIG. 9 is a front view schematically showing the internal structure of a transfusion pump according to the first embodiment of the present invention, and FIG. 10 is a left-hand side view schematically showing the internal structure of the first embodiment. In this embodiment, a plurality of fingers 41 are arranged in the axial direction of a liquid supply tube 40 formed of a soft synthetic resin or the like. The fingers 41 have strip-like heat absorbing portions 41a extending substantially horizontally, raised portions 41b formed by bending the heat absorbing portions 41a and extending vertically, and acting portions 41c formed by again bending the forward end portions of the raised portions 41b and extending horizontally. The heat absorbing portions 41a and the raised portions 41b are formed of a good conductor of heat such as copper or a copper alloy, and the acting portions 41c are formed as bimetals in which two kinds of metal having different thermal expansion coefficients are stacked together.

The above-mentioned liquid supply tube 40 is arranged below the acting portions 41c, and this liquid supply tube 40 is supported by a support plate 42. The support plate 42 is mounted on a base 44 through the intermediation of springs 43. In this embodiment, the liquid supply tube 40 is a transparent resin tube having a bore of approximately 0.1 mm. While conventional liquid supply tubes have a bore of not less than approximately 0.4 mm, in this embodiment, the bore is reduced so as to reduce the size of the drive section and the enhance the flexibility of the tube. Further, the wall thereof is thin.

The lower surfaces of the heat absorbing portions 41a of the fingers 41 are respectively in contact with a plurality of heat generating portions 45a formed on the surface of a thermal array 45. The upper surfaces of the heat absorbing portions 41a are in contact with a heat dissipating member 46 formed of a good conductor of heat such as copper. The heat dissipating member 46 may be connected to a heat dissipating fin or the like (not shown). The thermal array 45 is electrically connected to flexible circuit board 47.

As shown in FIG. 11, each heat generating portion 45a of the thermal array 45 is formed as follows: a heat resistant layer 451 consisting of inorganic glass or the like is formed on a ceramic base 450, and a heat generating resistant layer 452 consisting of a thin film of $Ta_2N$ is formed on this heat resistant layer 451. The heat generating resistant layer 451 is in contact with wiring layers 453 and 454 consisting of Al or the like. Further, an insulating protective layer 455 consisting of silicon oxide, tantalum oxide or the like is formed on these layers. The wiring layers 453 and 454 are connected to a head driving circuit of a control unit (not shown) through a wiring pattern formed on the flexible circuit board 47. The plurality of heat generating portions 45a, constructed as described above, are arranged on the surface of the base 450, and the heat generating portions 45a thus arranged are respectively in contact with the heat absorbing portions 41c of the plurality of fingers 41.

The heat absorbing portions 41c of the fingers 41 are held between the heat generating portions 45a of the thermal array 45 and the heat dissipating member 46. To achieve an improvement in terms of assembly and maintenance, it is desirable that the heat absorbing portions 41c be not firmly attached to the heat generating portions 45a and the heat dissipating member 46 but simply in press contact therewith.

In this embodiment, electricity can be supplied independently to each of the plurality of heat generating portions 45a of the thermal array 45 by a control signal from a control unit (not shown). When a heat generating portion 45a generates heat by supplying electricity thereto, the finger 41 which is in contact therewith is heated, and the acting portion 41c is bent downwards as indicated by the dotted line in FIG. 10. As a result of the downward bending of the acting portion 41c, the liquid supply tube 40 is depressed from above and deforms in such a way as to be crushed.

When the supply of electricity to the heat generating portion 45a is stopped, the finger 41 is cooled by the heat dissipating member 46, and the temperature of the acting portion 41c is lowered, so that the acting portion is restored to the position indicated by the solid line in FIG. 10 from the position indicated by the dotted line.

As indicated by the dotted lines in FIG. 9, in this embodiment, the acting portions 41c of the plurality of fingers 41 are periodically heated and driven with the phase being staggered little by little, which makes it possible for the portion A of the acting portion C which depresses the liquid supply tube to be sequentially shifted to the right as seen in the drawing, whereby it is possible to convey the liquid medicine in the liquid supply tube 40 to the right as seen in the drawing.

In this embodiment, the fingers 41 are deformed by thermally driving them to convey the liquid medicine in the liquid supply tube 40, so that the operating portions are the acting portions 41c only, and no large-sized power drive source or power transmission mechanism is needed. Thus, the structure is very simple and easily allows a reduction in size. At the same time, the number of parts is reduced, and the assembly is simplified, whereby the production cost can be reduced. Further, since it is not necessary to use a component which involves mechanical operation such as an electric motor, gear, cam and link, the noise can be reduced.

While in the above embodiment the acting portions 41c of the fingers 41 are formed as bimetals, it is also possible to form the fingers 41 of a shape memory alloy, the acting portions 41c being deformed by heating. Examples of the shape memory alloy include a Ti—Ni type alloy, Cu—Zn type alloy, Ni—Al type alloy, Fe—Mg type alloy and other three element type alloys. Basically, it is desirable for the thermally deformable member to be one which undergoes a reversible change. However, it is also possible to adopt an arrangement in which deformation in one direction is effected by heating or cooling, and in which this deformation is restored to the former state by a mechanism which allows a reversible deformation such as a spring or a plunger type solenoid.

Second Embodiment

Next, a second embodiment of this invention will be described with reference to FIG. 12. In this embodiment, fingers 41 which are substantially the same as those of the first embodiment are used. A thermal array 55 and a cooling member 56 are arranged along the heat absorbing portions 41a of the fingers 41, these components coming into contact with the lower surfaces of the heat absorbing portions 41a. A plurality of heat generating portions 55a are arranged above the thermal array 55, and the heat absorbing portions 41a of the fingers 41 are respectively in contact with these heat generating portions 55a.

The cooling member 56 consists of a thermal electric device utilizing the Peltier effect or the like. When electricity is supplied thereto, a plurality of protrusions 56a formed on the upper surface thereof independently absorb heat and dissipate it. This cooling member 56 is electrically connected to a flexible circuit board 57 together with the thermal array 55, and this flexible circuit board 57 is electrically connected to a control circuit (not shown).

In this embodiment, electricity is supplied to the heat generating portions 55a of the thermal array 55 to generate heat, making it possible to heat the fingers 41. After the heat generation of the heat generating portions 55a is stopped, electricity is supplied to the protrusions 56a of the cooling member 56, whereby heat can be absorbed by the fingers 41. Thus, the deformation of the fingers 41 and the restoration to the original configuration thereof can be effected quickly and reliably.

Further, the fingers 41 may be deformed either by the heating by the thermal array 55 or by the cooling by the cooling member 56. For example, it is possible to deform the fingers 41 through cooling by the cooling member 56 and restore them to the original configuration through heating by the thermal array 55.

Third Embodiment

Next, a third embodiment of the present invention will be described with reference to FIG. 13. In this embodiment, a finger 61 comprises a heat absorbing portion 61a, a connecting portion 61b and an acting portion 61c. One heat plate 64 an electrothermal element based on the Peltier effect or the like is in contact with the heat absorbing portion 61a, and the other heat plate 63 of the electrothermal element is in contact with a heat dissipating member 60.

The electrothermal element comprises an electrode layer 65 formed on the upper surface of the heat plate 63, and an electrode layer 66 formed on the lower surface of the heat plate 64, and p-type semiconductor layers 67 and n-type semiconductor layers 68 are arranged alternately. That is, the electrothermal element constitutes a module in which, as shown in FIG. 13, electrical connection is repeatedly effected sequentially in the order: the electrode 65, the n-type semiconductor layers 68, the electrode layer 66, and the p-type semiconductor layers 67.

Both the electrode layers 65 and 66 are formed so as to effect electrical connection between adjacent p-semiconductor layers 67 and n-type semiconductor layers 68. When a current is caused to flow between the electrode layer 65 or 66 at the right-hand and left-hand ends, transmission of heat is generated between the heat plates 63 and 64 by the electrothermal effect. When the current flowing between the electrode layers 65 and 66 is set to a certain direction, heat is transmitted from the heat plate 65 to the heat plate 66 as is well known, and the finger 61 is heated through the heat generation of the heat plate 66. On the other hand, when the direction of the current is reversed, heat is transmitted from the heat plate 66 to the heat plate 65, and the heat plate 66 takes heat from the finger 61, whereby the finger 61 is cooled.

In this way, in this embodiment, the finger 61 can be heated or cooled according to the direction of the current flowing through the electrothermal elements, and the deformation of the acting portion 61c of the finger 61 and the resotration to the former state thereof can be furthered by the heating and cooling, whereby it is possible to operate the finger 61 quickly and reliably to depress the liquid supply tube as in the above-described embodiment. A plurality of combinations of fingers and electrothermal elements as shown in FIG. 13 are arranged in the direction in which the liquid supply tube extends, and, by driving each electrothermal element, it is possible to individually control a plurality of fingers.

Fourth Embodiment

Next, a fourth embodiment of the present invention will be described with reference to FIGS. 14 through 16. In this embodiment, a plurality of fingers 62 made of the same material as the fingers 61 of the third embodiment are in contact with the electrothermal elements based on the Peltier's effect or the like. In this embodiment, the base portion of each finger 62, formed in a strip-like configuration, is divided into a first branch portion 62a and a second branch portion 62b. The first branch portion 62a is in contact with an upper heat plate 64', and the second branch portion 62b is in contact with a lower heat plate 63', as in the above-described third embodiment. However, a plurality of electrothermal module rows are arranged in a direction perpendicular to the plane of FIG. 14 and connected in a matrix-like fashion; the first branch portion 62a and the second branch portion 62b of a finger 62 are connected different electrothermal module rows.

The electrothermal elements comprises electrode layers 65' and 66' held between the heat plates 63' and 64', p-type semiconductors 67' and n-type semiconductors 68'. The electrothermal element comprises a plurality of electrothermal module rows in which electrical connection is repeatedly effected in the order: the electrode layer 65', the n-type semiconductor layers 68', the electrode layer 66', and the p-type semiconductor layers 67' along the direction in which the first branch portion 62a and the second branch portion 62b extend. The plurality of electrothermal module rows are arranged in a direction perpendicular to the plane of FIG. 14. As shown in FIG. 15, these plurality of electrothermal module rows are electrically connected in the horizontal direction perpendicular to the direction in which the first branch portion 62a and the second branch portion 62b extend such that connection is repeatedly effected in the order: the electrode layers 65', the n-type semiconductor layers 68', the electrode layers 66', and the p-type semiconductor layers 67'.

In FIG. 15, the portions of the electrothermal module rows of the electrothermal elements which correspond to four fingers are indicated by numerals with numbers 1 through 4 in parentheses. Each finger is in thermal contact with three electrothermal module rows. That is, of the four fingers 62, the first branch portion 62a(1) is in contact with the electrode layers 66'(1) through the intermediation of the heat plate 64', and this n-type semiconductor layer 68' is joined to the electrode layer 65'(0) on the heat dissipating member 69a. Further, the electrode layer 66'(1) is also joined to the p-type semiconductor layer 67', and this p-type semiconductor layer 67' is joined to the electrode layer 65'(1) formed on the heat plate in contact with the second branch portion 62b(1) of the first finger 62. This electrode layer 65'(1) is also joined to another n-type semiconductor layer 68', and this n-type semiconductor layer 68' is joined to the electrode layer 66'(2) formed on the lower surface of the heat plate 64' in contact with the first branch portion 62a(2) of the second finger. Further, this electrode layer 66'(2) is also joined to another p-type semiconductor layer 67', and this p-type semiconductor layer 67' is joined to the electrode layer 65'(2) formed on the heat plate 63' in contact with the second branch portion 62b(2) of the second finger. Similarly, regarding the third finger and the fourth finger also, they are in contact with joint units of the electrode layers 65'(3), 65'(4), 66'(3), 66'(4) and the p-type semiconductor layer 67', the n-type semiconductor layer 68'.

With respect to each of the n-type semiconductor layers 68' and the p-type semiconductor layers 67' shown in FIG. 15, the electrothermal module row shown in FIG. 14 extends in a direction perpendicular to the plane of the drawing. In these electrothermal module rows, the p-type semiconductor layers 67' and the n-type semiconductor layers 68' are arranged alternately and repeatedly, as shown in FIG. 14. In the electrothermal module row in which the n-type semiconductor layer 68' appears in FIG. 15 (the row extending in the direction of the plane of FIG. 15), the position of the n-type semiconductor layer and the position of the p-type semiconductor layer are reverse when compared with the electrothermal module in which the p-type semiconductor layer 67' appears in FIG. 15. That is, in the two adjacent electrothermal module rows, the conduction types of the semiconductor layers included therein are opposite to each other.

As shown in FIG. 15 and 16, the first branch portion 62a and the second branch portion 62b of the finger 62 are arranged so as to be horizontally deviated from each other so that they are two-dimensionally partly overlap. A part of the second branch portion 62b of the finger 62 two-dimensionally overlap the first branch portion of the adjacent finger, and a part of the first branch portion 62a of the finger 62 two-dimensionally overlap the second branch portion of the adjacent finger.

In this embodiment, in the electrothermal module row at the left-hand end shown in FIG. 15, of the electrode layers 65'(0) (a plurality of them are divisionally arranged in the direction perpendicular to the plane of the drawing), that electrode layer 65'(0) which is at the bottom with respect to the plane of the drawing (the left-hand end in FIG. 14) is supplied with high potential, and that electrode layer 65'(0) which is nearest to the reader with respect to the plane of the drawing (the right-hand end in FIG. 14) is supplied with low potential, whereby, in the electrothermal module, it is possible, as shown in FIG. 14, to flow a current in a zigzag fashion through the p-type semiconductor layers 67' and the n-type semiconductor layers 68' arranged alternately between the electrode layer 65'(0) and the electrode layer 66'(1), with the result that heat is absorbed from the heat dissipating member 69a and transmitted to the first branch portion 62a(1) of the first finger to heat the first finger.

Next, when the supply of electricity to the electrode layer 65'(0) is stopped and electricity is supplied to the electrode layer 65'(1) in a similar manner, the next electrothermal module row (the second row from the left-hand side of FIG. 15) formed between the electrode layer 65'(1) and the electrode layer 66'(1) absorbs heat from the first branch portion 62a(1) and transmits heat so as to dissipate it to the second branch portion 62b(1). The still next electrothermal module row formed between the electrode layer 65'(1) and the electrode layer 66'(2) conversely absorbs heat from the second branch portion 62b(1) of the first finger and transmits heat so as to dissipate it to the first branch portion 62a(2) of the second finger. Due to this arrangement, heat is transmitted generally from the first finger to the second finger; the second finger is heated simultaneously with the cooling of the first finger.

Similarly, when the supply of electricity to the electrode layer 65'(1) is stopped and electricity is supplied to the electrode layer 65'(2), the second finger is cooled, and the third finger is heated. In this way, it is possible to cool the once heated finger and, at the same time, gradually heat the adjacent finger. In this embodiment, heat is taken from a previously heated finger and heat is supplied to the finger to be heated next, so that it is possible to successively operate the fingers solely through transmission of heat, whereby it is possible to control and drive very efficiently. Although it is possible to individually provide each finger with an electrothermal module for drive, it is possible, as in this embodiment, to operate the fingers while effecting heat exchange between adjacent fingers, whereby there is no need to effect heat exchange between the interior and exterior of the device, thereby preventing overheating, condensation, etc. of the device.

In this embodiment, a plurality of electrothermal module rows are connected together in a direction perpendicular to the plane of FIG. 14, as shown in FIG. 15. However, instead of this arrangement, it is possible to simply arrange the individual electrothermal units, connected together as shown in FIG. 15, in parallel in a direction perpendicular to the plane of the drawing, and to supply electricity to each of the electrothermal units, thereby achieving the same effect.

Further, in this embodiment, when the electrode layer to which electricity is supplied is changed, heat is transmitted from the first branch portion, which has been heated, to the second branch portion, and from the second branch portion to the first branch portion of the adjacent finger. However, it is also possible to simply stop the heating of the first branch portion by the Peltier effect and to generate transmission of heat from the second branch portion to the first branch portion of the adjacent finger. As in this embodiment, this method also makes it possible to simultaneously effect the cooling of the finger after the stopping of heating and the heating of the adjacent finger.

EMBODIMENTS IN THE THIRD ASPECT OF THE PRESENT INVENTION

In the third aspect of the invention, there is provided a liquid supply tube for use in a transfusion pump. It relates to the structure of a liquid supply tube formed by firmly fixing together two component members.

First Embodiment

FIG. 17 is a perspective view schematically showing the structure of a liquid supply tube according to the present invention, and FIG. 18 is a sectional view showing the structure of the liquid supply tube. This liquid supply tube 80 is formed by joining a hard plate-like member 81 formed of a hard synthetic resin with a flat elastic plate-like member 82 formed of an elastic, flexible synthetic resin at joint surfaces B1 in the edge portions with respect to the width direction. The joining is effected by adhesion using an adhesive, welding using heat or oscillation (ultrasonic wave), etc.

The hard plate-like member 81 comprises an extended groove portion 81a at the center with respect to the width direction having a semi-circular sectional configuration, and a pair of flat portions 81b protruding on either side of the extended groove portion 81a. Inside the extended groove portion 81a, there is formed a liquid passage B2 defined between the groove portion and the inner surface of the elastic plate-like member 82.

In this liquid supply tube 80, a liquid passage B2 for liquid medicine is secured by the hard plate-like member 81 having the extended groove portion 81a, and liquid medicine can be conveyed by deforming the flexible elastic plate-like member 82. That is, as shown in FIG. 19, the elastic plate-like member 82 is depressed from outside by a depression member 83 such as a roller or finger, whereby it is possible to press the elastic plate-like member against the inner surface of the extended groove portion 81 of the hard plate-like member 81; by moving the depressed portion in the direction in which the liquid passage B2 extends, it is possible to move the liquid medicine inside the liquid supply tube.

For example, when forming a rotary type transfusing device, the hard plate-like member 81 is curved in an arcuate form along the rotating direction of the rotation arm to which a roller is attached, and the elastic plate-like member 82 is joined so as to be arranged inside the curved form. When forming a finger type transfusing device, a linear liquid passage B2 is formed as shown in FIG. 17, and fingers are arranged on the elastic plate-like member 82 side.

In this case, when the forward end portion 83 of the depression member such as roller or finger has a curved configuration substantially corresponding to the inner surface of the extended groove portion 81a of the hard plate-like member 81, it is possible to deform the elastic plate-like member 882 so as to be substantially in conformity with the inner surface of the extended groove portion 81a through the depression of the depression member 83, so that it is possible to control and maintain the speed at which the liquid medicine is supplied with high accuracy and stability.

In the above-described liquid supply tube, the hard plate-like member 81 and the elastic plate-like member 82 can be easily and separately formed by injection molding, extrusion, or the like; even when the size of the liquid passage B2 is small, the production is easier as compared with the case of a tubular member produced by extrusion or the like. Accuracy in form is easily achieved if the diameter of the liquid passage B2 is small. Further, a reduction in production cost can be achieved.

Further, since the component members may have a simple configuration, there is little limitation in terms of material. In particular, the characteristics of the elastic plate-like member 82, such as elasticity, flexibility and durability can be improved. In this embodiment, the elastic plate-like member 82 has a parallel and flat configuration, so that it is easy to produce. The production can be conducted with a high quality material.

Further, when compared with the conventional tubular liquid supply tube (which is the strongest against external forces), the requisite stress for closing the liquid passage is smaller. Further, it is not apt to assume an unnatural closing configuration, so that it is possible to reduce the driving force, and reduce the size of the driving mechanism and the energy consumed.

While in the above-described embodiment one of the component members is formed as a hard plate-like member 81, it is also possible to form both component members of an elastic material by supporting by a support member or the like. Further, it is not absolutely necessary for the component members to be plate-like members. For example, instead of the hard plate-like member 81, it is also possible to use a block member having an extended groove portion on its surface. Further, instead of the elastic plate-like member 82, it is possible to adopt members of various configurations partly equipped with a flat plate-like portion.

In this embodiment, one of the two component members forming the liquid supply tube 80, the hard plate-like member 81 and the elastic plate-like member 82, i.e., the elastic plate-like member 82, is formed as a plate-like member having elasticity. Instead of thus providing one of the component members with a plate-like portion having elasticity, it is also possible to provide one of the component members with a plate-like portion having little elasticity. In this case, the depression member 83 and the plate-like portion are firmly attached to each other by adhesion or the like and, in this condition, the depression member 83 is operated to increase and decrease the sectional area of the liquid passage B2 to thereby convey the liquid medicine.

Second Embodiment

Next, a second embodiment of this invention will be described with reference to FIGS. 20, 21 and 22. As shown in FIG. 20, the liquid supply tube 80' of this embodiment is formed by joining together a hard plate-like member 81 and an elastic plate-like member 82 similar to those of the first embodiment. On the inner surface of the elastic plate-like member 82 and at positions opposite to the extended groove portion 81a, a plurality of elastic protrusions 84 are arranged along the liquid passage B2. As shown in FIG. 21, these elastic protrusions 84 have a surface configuration substantially in conformity with the inner surface of the extended groove portion 81a. As shown in FIG. 22, when the outer surface of the elastic plate-like member 82 is depressed by a depression member 83, the elastic protrusion 84 abuts substantially snugly against the inner surface of the extended groove portion 81a and acts so as to close the liquid passage B2.

In this embodiment, the liquid passage B2 can be easily closed by the elastic protrusion 84, so that it is possible to reduce the driving force of the depression member and achieve a reduction in the size of the device and the power consumed. Further, since the liquid passage B2 can be closed by the elastic protrusion 84, the liquid passage B2 can be easily closed if the elastic plate-like member 82 is thin, so that it is possible to enhance the follow capacity with respect to the deformation of the elastic plate-like member 82.

Further, since in this embodiment the liquid passage B2 can be easily closed, the speed at which the liquid medicine is supplied can be controlled with accuracy, thereby making it possible to convey the liquid medicine in a stable manner. Further, since the deformation amount of the elastic plate-like member 82 can be reduced, there is less limitation in terms of the material of the elastic plate-like member 82 and, at the same time, the durability of the liquid supply tube can be enhanced.

Due to their elasticity, the elastic protrusions 84 deform with the elastic plate-like member 82, so that it is possible to close the liquid passage B2 more flexibly. The elastic protrusions 84 may be formed integrally with the elastic platelike member 82. Further, instead of the elastic protrusions 84, it is also possible to provide protrusions formed of a less elastic material such as metal.

In this embodiment, the liquid in the tube can be conveyed by depressing the liquid supply tube 80' by the depression member 83 as shown in FIG. 22. Instead of the elastic protrusions 84 arranged in the liquid supply tube 80', it is also possible to use magnetic members of substantially the same configuration; these magnetic members are vertically moved as seen in FIG. 22 by an electromagnet provided outside, whereby it is possible to convey the liquid medicine in the liquid supply tube 80' while deforming the elastic plate-like member 82. The electromagnet is arranged, for example, outside and below the extended groove portion 81a shown in FIG. 22, whereby the above-mentioned magnetic members fastened to the inner side of the elastic plate-like member 82 can be driven.

As described below, the liquid supply tube of the first and second embodiment can be used in the liquid medicine conveying section of a peristaltic transfusing device. Further, it can be used as a tube for conveying an arbitrary liquid; it can be used for the purpose off increasing and decreasing the flow section of a liquid by the mechanical stress or the electromagnetic stress as described above. In particular, is can also be used as a part of a valve body for cutting off the feeding out of a liquid.

Next, an example of the construction of a transfusing device (transfusion pump) using the liquid supply tube 80' of the above-described second embodiment will be described with reference to FIGS. 23, 24 and 25. On either side of the liquid supply tube 80', depression levers 92 each including a thermally deformable portion 92a consisting of bimetal are arranged alternately respectively in correspondence with the elastic protrusions 84 of the liquid supply tube 80'. Fastened to the forward end portion of the thermally deformable portion 92a of each depression lever 92 is a depression piece 94 having a gently protruding curved surface. The base portion of each depression lever 92 is divided into upper and lower sections 92b and 92c.

As shown in FIG. 24, a common electrothermal element 95 utilizing the Peltier effect or the like exists between the upper section 92b of one depression lever 92 and the lower section 92c of another depression lever 92 adjacent thereto on one side of the liquid supply tube. The heat dissipating portion 95a of the electrothermal element 95 is thermally in contact with the upper section 92b, and the heat absorbing portion 95b of the electrothermal element 95 is thermally in contact with the lower section 92c of the adjacent depression lever. Thus, on either side of the liquid supply tube, a plurality of electrothermal elements 95 existing between adjacent depression levers are arranged.

By causing a current to flow in a predetermined direction, each of the electrothermal elements 95 absorbs heat from the heat absorbing portion 95b shown in FIG. 23 and dissipates it from the heat dissipating portion 95a. In this way, each depression lever 92 is thermally in contact with two electrothermal elements: the electrothermal element in contact with the upper section 92b and the electrothermal element in contact with the lower section 92c. Thus, when electricity is supplied to the electrothermal element 95 which is in contact with the upper section 92b of the depression lever 92, the depression lever 92 is heated and, as shown in FIG. 25, the thermally deformable portion 92a of bimetal structure is downwardly bent, and the depression piece 94 downwardly depresses the outer surfaces of the elastic plate-like member 82. Then, the elastic plate-like member 82 depressed by the depression piece 94 downwardly depresses the elastic protrusion 84 provided inside to thereby close the liquid passage B2.

Next, the current flowing to the electrothermal element 95 in contact with the upper section 92b of the depression lever 92 is cut off and, at the same time, a current is caused to flow to the electrothermal element 95 in contact with the lower section 92c. Then, the depression lever 92, which has been heated, starts to be cooled. As the temperature of the depression lever 92 is gradually lowered, the thermally deformable portion 92a is gradually restored to the original state, and the elastic protrusion 84 retreats upwards, the liquid passage B2 starting to gradually open. At this time, the electrothermal element 95 which is in contact with the lower section 92c of the depression lever 92 comes into contact with the upper section 92b of the adjacent depression lever 992 and heats this adjacent depression lever 92, so that the thermaly deformable portion 92a of this adjacent depression lever 992 is gradually bent and starts to close the liquid passage B2. Thus, when a certain depression lever 92 is heated, another depression lever on the upstream side of the liquid passage is cooled, and when the certain depression lever 92 is cooled, another adjacent depression lever 92 on the downstream side of the liquid passage is heated, so that the depression levers 92 arranged from the upstream side to the downstream side of the liquid passage B2 are sequentially heated and cooled, and the position of the liquid passage B2 which is closed by the depression lever 92 is gradually displaced downwards.

Since a plurality of depression levers 92 are arranged on either side of the liquid supply tube 80', synchronous control is effected with the phase of the heating/cooling timing for the depression levers arranged on one side of the liquid supply tube 80' being shifted from the phase of the heating/cooling timing for the depression levers arranged on the other side of the liquid supply tube 80', whereby delay in the thermal response time of the individual depression levers 92 is avoided, thereby making it possible to convey the liquid medicine in the liquid supply tube 80' downwardly.

In this embodiment, the depression levers having a bimetal structure are deformed by heating and cooling of the electrothermal elements, so that there is not much mechanically operated portion, and it is possible to provide a driving mechanism having less noise, relatively free from failure and having high durability. Further, since the heat absorbing portions and heat dissipating portions of the electrothermal elements are joined to adjacent depression levers, and the depression levers are heated and cooled efficiently, so that there is provided a high energy efficiency, and the power consumed is reduced. Further, since the liquid supply tube is depressed by depression levers responding to heat, the depressing operation of the depression levers is effected smoothly, and no abrupt motion is generated, so that the durability of the liquid supply tube is further improved.

While in this construction example an electrothermal element is used as the heating/cooling means, it is also possible to adopt other types of heating means, such as an electric heater, and cooling means, such as ones using a heat dissipating plate, refrigerant, etc. Further, while in this construction example a bimetal structure is adopted as the heat responsive material, it is also possible to adopt other type of heat responsive material which reversibly deforms by heating and cooling, such as shape memory alloy.

While this construction example consists of a peristaltic transfusing device (transfusion pump) formed by using the liquid supply tube shown with reference to the second embodiment and, in particular, a finger type transfusion pump structure, it is also possible to adopt another finger type driving mechanism as the transfusing device using the first or second embodiment. Further, by providing a liquid supply tube in an arcuate form and a mechanism for rotating a rotating arm with roller at its both ends, it is possible to form a rotary type transfusion pump.

Third Embodiment

Next, a third embodiment of the liquid supply tube of the present invention will be described with reference to FIG. 26. This liquid supply tube 100 comprises a U-shaped block member 101 formed of a hard plastic or the like, and an elastic sheet attached to the upper surface of the block member 101. The block member 101 comprises a prism-like central portion, and a pair of end portions provided at the ends thereof and protruding downwardly. On the upper surface of the block member 101, there is formed an extended groove portion 101*a* having a semi-circular cross-sectional configuration. This extended groove portion end near the ends of the block member 101 and does not extend therethrough. From the end portions of the extended groove portion 101*a*, there extend downwardly connection holes 101*b*, which reach the lower surface of the end portions.

In this embodiment, the end portions of the liquld supply tube 100 is formed integrally with the block member 101, so that it is possible to appropriately design the end portion configuration for connection to a transfusion tube or the like without increasing the number of parts. While in this embodiment the end portions of the liquid supply tube 100 have a prism-like configuration, it may also have, for example, a tubular configuration, in conformity with the end portion configuration of the transfusion tube. Further, screw portions may be provided thereon.

FIG. 27 shows the configuration of a joint member 103 for joining a liquid supply tube with a semi-circular sectional configuration to a transfusion tube with a circular sectional configuration for use in the case in which no special end portion configuration as shown in FIG. 26 as in the case of a liquid supply tube having a circular sectional configuration as shown in FIGS. 24 and 25. An end portion 103*a* of the joint member 103 has a semi-circular cross-sectional configuration that can be fitted onto a liquid supply tube, and an end portion 103*b* thereof has a circular configuration that can be fitted onto a transfusion tube.

EMBODIMENTS IN THE FOURTH ASPECTS OF THE INVENTION

In the fourth aspect of the present invention, there is provided a transfusion pump which performs transfusion in a stable manner with a plurality of fingers, with the liquid medicine being pressurized on the upstream side.

FIG. 28 a sectional view schematically showing the construction of a transfusing device according to a first embodiment of the present invention. In this embodiment, liquid medicine is injected into a balloon 110 formed of an elastic material such as synthetic rubber, and the balloon 110 is held between upper and lower pressing plates 111 and 112 and pressurized at a predetermined pressure. The balloon 110 is connected to a flexible liquid supply tube 116 formed of a synthetic resin, and a support plate 121 is arranged on one side of this liquid supply tube 116. In the liquid supply tube 116, on the side opposite to the support plate 121, the forward end portion of a valve member 122 constituting an inlet valve and the forward end portion of a valve member 123 constituting a discharge valve are opposed to each other at an interval. Between the valve members 122 and 123, four pushers 124, 125, 126 and 127 are arranged in the direction in which the liquid supply tube 16 extends.

The valve members 122 and 123 and the four pushers 124, 125, 126 and 127 are caused to move toward and away from the liquid supply tube 16 by plunger type micro solenoids 128 (there are two of them) and 129 (there are four of them).

FIG. 29 is a right-hand side view of FIG. 28, showing the construction of the section for pressurizing the balloon 110. The balloon 110 is placed on the pressing plate 111 which is attached to the case of the transfusing device or which constitutes the bottom plate of the case, and the pressing plate 112 is placed on the balloon 110. The pressing plate 112 is connected to lower edge portions 114*a* of a cover 114 having a U-shaped sectional configuration by a rubber band 113. Thus, the balloon 110 is pressurized from above and below by the pressing plates 111 and 112, whereby a predetermined pressure is applied to the liquid medicine.

FIGS. 30 through 33 illustrate how the valve members 122 and 123 and the pushers 124, 125, 126 and 127, which constitute the transfusion pump, operate. First, as shown in FIG. 30, the valve member 123 on the downstream side protrudes toward the tube 116 and the valve member 122 on the upstream side and the pushers 124, 125, 126 and 127 are all drawn back. In this condition, the discharge valve is closed by the valve member 123.

Next, as shown in FIG. 31, the valve member 122 protrudes toward the liquid supply tube 116, and the upstream side of the liquid supply tube 116 is shut. Here, liquid medicine pressurized by the pressurizing means is trapped in that section of the liquid supply tube 116 which is between the valve member 122 and the valve member 123.

Next, as shown in FIG. 32, the valve member 123 is drawn back and the pusher 124 protrudes. When the valve member 123 is drawn back, the volume of that section of the liquid supply tube 116 which has been depressed by the valve member 123 increases, so that there is a fear that reverse flow of liquid medicine is generated in the liquid supply tube 116 backwards from the downstream side from the portion which has been depressed by the valve member 123 or that the liquid medicine will be partially under negative pressure to generate a bubble. In view of this, the increase in the volume of the liquid supply tube due to the drawing back of the valve member 123 (and the change in pressure inside the tube attributable thereto) is compensated for by the protrusion of the pusher 124, thereby mitigating the generation of negative pressure, bubbles, etc.

Next, as shown in FIG. 33, the pushers 125, 126 and 127 are caused to protrude to push out the liquid medicine inside the liquid supply tube 116 downwardly, whereby the liquid medicine is discharged. Although all the pushers 125, 126 and 127 may be simultaneously caused to protrude, it is more desirable for the pushers to be sequentially protruded with shifted timing starting from the upstream side pusher 125 and ending with the downstream side pusher 127 in order to convey the liquid medicine more smoothly.

When the discharge of the liquid medicine has been completed as described above, the valve member 123 is caused to protrude again as shown in FIG. 30 to close the discharge valve, and the upstream side valve member 122 and the pushers 124, 125, 126 and 127 are drawn back to take liquid medicine from the upstream side into the liquid supply tube 116.

It is desirable that the valve members 122 and 123 and the pushers 124, 125, 126 and 127 be formed so as to completely close the liquid supply tube 116 in order that the flow of liquid medicine in the liquid supply tube 116 may be completely cut off when they protrude. However, even if the liquid supply tube 116 is not completely closed by the valve members and the pushers and the flow of liquid medicine is not completely cut off, the same effect as described above can be obtained if the closed state of the liquid supply tube 116 is substantially complete, and the influence of the pressure of the liquid medicine on the upstream side is hardly transmitted to the downstream side.

Regarding the valve member 122 in FIGS. 32 and 33, and the pushers on the upstream side when the pushers on the downstream side are protruding, they need not be protruding as shown in the drawings since the pressure of the liquid medicine is cut off by the pushers on the downstream side cutting off the interior of the liquid supply tube 116; they may be drawn back immediately after the protruding of the pushers on the downstream side.

While in the above pump structure formed by the support plate, the valve members and the pushers, operation is effected by the two valve members and the four pushers opposed to the support plate, there is no need to discriminate between the valve members constituting the inlet valve and the discharge valve, and the pushers constituting the discharge mechanism; they may all consist of the same members. The minimum number of these valve members and pushers is three.

Further, while in the above embodiment the valve members and the pushers are driven by solenoids, the valve members and pushers may also be driven by mechanical parts such as cams or air cylinders.

In this embodiment, the liquid medicine is constantly pressurized at a constant pressure by the balloon and the pressurizing mechanism (111, 112, 113 and 114) for the balloon, and a fixed amount of this pressurized liquid medicine isAbrought into the pump at one time by the valve members and pushers, and the liquid medicine thus taken in is discharged. Thus, the minimum requisite number of valve members and pushers is three, so that the number of parts can be substantially reduced as compared with the conventional finger type transfusion pump.

There is no need for the liquid medicine to be pressurized at a fixed pressure; for example, the liquid pressurizing means may be formed solely by the balloon 110. Further, the liquid pressurizing means may be of a piston type in which, for example, a predetermined stress is applied to the rod of the cylinder, or one which utilizes an air cylinder.

Further, since the liquid medicine is taken in and discharged from the pump formed by the support plate, the valve members and the pushers, the amount of liquid medicine discharged is determined with high accuracy, and the speed at which the liquid medicine is injected can be set with high accuracy. Further, it is possible to inject a minute amount of liquid medicine. In this case, to increase the speed at which the liquid medicine is supplied, the operating period of the valve members and the pushers is reduced to thereby effect high speed operation.

In this method, by changing the number and width of the valve members and the pushers, it is possible to easily adjust the amount of liquid medicine discharged at one time. Further, it is possible to control the supply pressure of the liquid medicine by the operating period of the valve members and the pushers, not depending on the pressurizing force for the liquid medicine on the upstream side. Thus, it is possible to supply the liquid medicine at high pressure.

In the conventional peristaltic transfusing device, the liquid supply tube is endowed with a sufficient degree of elasticity, so that the liquid supply tube deforms when depressed by the fingers in correspondence with the positions of the fingers, whereby the liquid medicine is conveyed. In this embodiment, in contrast, pressurized liquid medicine is substantially trapped in a predetermined region of the liquid supply tube, and this trapped liquid medicine is discharged, so that there is no need for the liquid supply tube to have elasticity; it has only to have a sufficient degree of flexibility. Thus, in this embodiment, the wall of the liquid supply tube may be thin, so that the power loss of the pump is reduce, thereby enhancing the pump efficiency. Further, the diameter of the liquid supply tube can be easily diminished, whereby it is possible to easily inject a minute amount of liquid medicine.

EMBODIMENTS IN THE FIFTH ASPECT OF THE INVENTION

The fifth aspect of this invention relates to the construction of a transfusion pump equipped with a diaphragm which performs transfusion with the liquid medicine being pressurized on the upstream side.

Next, an embodiment of the transfusing device of this invention will be described with reference to FIGS. 34 through 38. In this embodiment, a power source 131 such as a battery and a circuit board 132 on which an electronic circuit including a control circuit is formed are accommodated in a case 130. Further, a transfusion pump controlled by the control circuit is formed.

This transfusion pump comprises a diaphragm 133 consisting of metal, semiconductor, ceramic, synthetic resin or the like and formed by stamping, photolithography, sintering, resin molding or the like, and a base 134 which consists of a similar material and is formed by any one of the above-mentioned techniques or machining and which has an inlet hole 134a and a discharge hole 134b.

The diaphragm 133 comprises a valve portion 133a formed at a position corresponding to the inlet hole 134a of the base 134, a discharge deformation portion 133b formed at the center, and a valve portion 133c formed at a position corresponding to the discharge hole 134b of the base 134. The valve portions 133a and 133c are formed as thick walled portions surrounded by thin walled portions that are easily deformed. At the lower ends thereof, there are formed valve body portions consisting of elastic members formed of synthetic rubber or the like such as silicone rubber which does not react with chemicals. These valve body portions are firmly attached to the diaphragm 133 by adhesion, coating or the like.

The valve portions 133a and 133b are formed such that they open and close the inlet hole 134a and the discharge hole 134b by micro actuators 135 and 137, respectively, mounted on the circuit board 132. Further, the discharge deformation portion 133b is formed as a thin walled portion having a large area, and is similarly largely deflected to the interior and exterior of the pump chamber by a micro actuator 136 mounted on the circuit board 132.

The micro actuators 135, 136 and 137 may consist of various plunger type solenoids, piezoelectric actuators, micro motors, air cylinders, hydraulic cylinders or the like. Further, around the discharge hole 134b of the base 134, there are mounted a flow rate sensor 138 and a bubble sensor 139.

Connected to the inlet hole 134a of the base 134 is a liquid medicine pressurizing mechanism consisting of an elastic balloon 110.

First, as shown in FIG. 35, in this embodiment, the valve portion 133a and the discharge deformation portion 133b is kept at the raised position, and the valve portion 133c is lowered by pressing it by the micro actuator 137 to close the discharge hole 134b. In this condition, liquid medicine is introduced into the pump from the balloon 110 (not shown) at a predetermined pressure. Next, as shown in FIG. 36, the valve portion 133a is lowered by depressing it by the micro actuator 35 to close the inlet hole 134a. In this condition, the liquid medicine introduced into the pump is trapped therein at the pressure at which it has been supplied.

Next, as shown in FIG. 37, the depression by the micro actuator 137 is canceled, and the valve portion 133 is restored to the raised position by the elasticity of the diaphragm 133 to open the discharge hole 134b. At this time, to prevent reverse flow of the liquid medicine due to the raising of the valve portion 133c, the micro actuator 136 is operated to slightly push down the discharge deformation portion 133b.

Next, as shown in FIG. 38, the micro actuator 136 is operated to greatly push down the discharge deformation portion 133b to discharge the liquid medicine in the pump through the discharge hole 134b. When the discharge of the liquid medicine has been completed, the valve portion 133c is depressed by the micro actuator 137 to close the discharge hole 134b again. After this, the valve portion 133a is raised to open the inlet hole 134a, and the discharge deformation portion 133b is restored to the original state, whereby the condition as shown in FIG. 35 is restored.

In this embodiment also, as in the embodiment in the fourth aspect of the invention, the liquid medicine can always be conveyed in a pressurized state, so that no fluctuations in the pressure of the liquid medicine with passage of time are generated, and the device can be used in a stable state. Further, the liquid medicine is not placed under negative pressure, and few bubbles are generated. Further, the flow rate can be controlled with high accuracy, and it is possible to discharge a minute amount of liquid medicine. Further, the size of the device can be easily reduced.

In the above embodiment, by making the diaphragm 133 and the base 134 detachable with respect to the case 130, replacement, cleaning, inspection, etc. are facilitated.

EMBODIMENTS COMMON TO THE ASPECTS OF THE INVENTION

Finally, a specific example of the general construction of a transfusing device which is commonly applicable to the above aspects of the invention will be described with reference to FIGS. 39 and 40. FIG. 39 is a schematic diagram showing the general construction of the transfusing device. A discharge mechanism 140, constructed as shown with reference to the above-described embodiments, is arranged along the liquid supply tube 116 that can be connected to a liquid medicine cartridge 141 containing a pressurizing mechanism composed of the balloon 110 and the pressing plates 111 and 112. On the downstream side of the discharge mechanism 140, there is mounted a micro sensor 142, which detects the presence of a bubble in the liquid supply tube 116, the stopping of the liquid medicine in the liquid supply tube 116, etc.

The operating section such as the discharge mechanism 140 is controlled by a central control unit 143. The central control unit 143 transmits a control signal to a drive circuit 144, and operates the discharge mechanism 140 by an actuator 145 formed as a solenoid, micro actuator or the like. The actual operating speed of the discharge mechanism 140 is detected by a detecting circuit 149 consisting of an optical sensor or the like. The drive signal transmitted from the drive circuit 144 to the actuator 145 and the detection signal transmitted from the detecting circuit 149 are introduced to a pulse counter 146, and the difference therebetween is counted by the pulse counter and fed back to the central control unit 143.

A predetermined potential is supplied to the drive circuit 144 from a power source circuit 148 which is supplied with a predetermined potential which is supplied with power from a power source 147 such as a battery.

Connected to the central control unit 143 are an operating section 151, an alarm device 152, an external terminal connecting section 153, and a display device 154. When during the conveyance of the liquid medicine a bubble in the liquid medicine or the stopping of liquid medicine is detected by the above micro sensor 142, the central control unit 143 gives an alarm from the alarm device 152 consisting of a speaker or the like. Further, the central control unit 143 inputs signals from other control apparatus or measurement apparatus from the external terminal connecting section 153, and, in accordance with the signals, controls the injection speed, injection time, etc. of the liquid medicine. Further, the central control unit 143 constantly displays the liquid medicine injection speed, integral of injection time, etc. through the display device 154.

FIG. 40 is a schematic diagram showing the appearance of this transfusing device. There is provided a plastic case 150 designed to be of a size which can be held by hand, and the liquid supply tube 116 is inserted into the case. The discharge mechanism 140 and the micro sensor 142 arranged along the liquid supply tube 116. Further, the central control unit 143, the drive circuit 144, the actuator 145, the pulse counter 146 and the power source circuit 148 are formed on the circuit board to form a circuit block 155.

Further, the case 150 accommodates the power source (battery) 147 and the alarm device 152. On the surface of the case, there are arranged the operating section 151 consisting of a plurality of push-button switches, the external terminal connecting section 153 consisting of mini-jacks or the like, and the display section 154 consisting of a liquid crystal panel or the like.

In the upper section of the case 150, there is provided an opening 150a, into which the liquid medicine cartridge 141 can be detachably inserted. As shown in FIG. 39, the liquid medicine cartridge 141 is provided with a joint section 141a. When the liquid medicine cartridge 141 is inserted into the opening 150a of the case 150, it is automatically connected to a joint receiving section (not shown) provided inside the case 150. The forward end of the liquid supply tube 116 is connected to the joint receiving section. When the liquid medicine cartridge 141 is attached, the joint section 141a thereof communicates with the liquid supply tube 116.

As a whole, this transfusing device can be formed in a size that can fit in the palm of a hand or be accommodated in a pocket. This is made possible by the discharge mechanism of a simple structure shown with reference to the above embodiments. In this transfusing device, there is no need for the liquid medicine cartridge to be completely accommodated in the case 150. As shown in FIG. 40, the main portion of the cartridge is formed so as to protrude to the exterior of the case 150, whereby it is possible to further reduce the size of the case 150. In this case, a portable liquid medicine cartridge which is further reduced in size as needed is attached, whereby it is possible for the size of the entire device to be further reduced. Such a reduction in the size of the transfusing device is nowadays much required in medical facilities, and the present invention provides a quite remarkable effect for medical use.

Industrial Applicability

As described above, in accordance with the present invention, a transfusing device, in particular, a transfusion pump, can be produced in a simpler form by reducing the number of parts, simplifying the part structure, etc., so that it is possible to achieve a reduction in production cost. Further, it is possible to reduce the size and weight of the transfusing device. For example, it is possible to form the device as a portable transfusing device and to inject a minute amount of liquid medicine into the body of the patient with high accuracy.

What is claimed is:

1. A transfusing device comprising:

a flexible liquid supply tube;

a support member supporting the liquid supply tube from one side; and a rotary drive member disposed adjacent to the liquid supply tube on an opposite side of the support member and comprising:

a rotation shaft arranged substantially parallel to a direction in which the liquid supply tube extends, at least one pressing protrusion for pressurizing the liquid supply tube is integrally provided on an outer peripheral surface of the rotary drive member, and wherein the at least one pressing protrusion is spirally arranged on the outer peripheral surface of the rotary drive member; and a flexible sheet provided between the liquid supply tube and the outer peripheral surface of the rotary drive member, wherein the flexible sheet is a partition formed of thin material, and the partition comprises:

a section having a plurality of slits formed and arranged in a direction in which the liquid supply tube extends, the slits forming a plurality of strip-like lead members; and a base portion where no slits are formed, wherein in said base portion said partition is fixed to a support plate.

* * * * *

UNITED STATES PATENT AND TRADEMARK OFFICE
CERTIFICATE OF CORRECTION

PATENT NO. : 6,270,326 B1
DATED : August 7, 2001
INVENTOR(S) : Hiroshi Kuriyama

It is certified that error appears in the above-identified patent and that said Letters Patent is hereby corrected as shown below:

<u>Title page,</u>
Item [54], correct "Transfusion Device And Liquid Supply Tube" to
-- Transfusing Device Having A Flexible Sheet To Prevent Tangential Rotation Of The Supply Tube --.

Signed and Sealed this

Twelfth Day of March, 2002

*Attest:*

JAMES E. ROGAN
*Attesting Officer           Director of the United States Patent and Trademark Office*